US012600865B2

(12) United States Patent
Aizenberg et al.

(10) Patent No.: US 12,600,865 B2
(45) Date of Patent: Apr. 14, 2026

(54) ANTI-FOULING ENDOSCOPES AND USES THEREOF

(71) Applicants: President and Fellows of Harvard College, Cambridge, MA (US); Beth Israel Deaconess Medical Center, Inc., Boston, MA (US)

(72) Inventors: Joanna Aizenberg, Boston, MA (US); Steffi Sunny, Cambridge, MA (US); Nicolas Vogel, Erlangen (DE); Adnan Majid, Boston, MA (US); George Cheng, Boston, MA (US); Michael Aizenberg, Boston, MA (US)

(73) Assignees: President and Fellows of Harvard College, Cambridge, MA (US); Beth Israel Deaconess Medical Center, Inc., Boston, MA (US)

( * ) Notice: Subject to any disclaimer, the term of this patent is extended or adjusted under 35 U.S.C. 154(b) by 763 days.

(21) Appl. No.: 16/096,220

(22) PCT Filed: Apr. 27, 2017

(86) PCT No.: PCT/US2017/029858
§ 371 (c)(1),
(2) Date: Oct. 24, 2018

(87) PCT Pub. No.: WO2017/189855
PCT Pub. Date: Nov. 2, 2017

(65) Prior Publication Data
US 2019/0136070 A1 May 9, 2019

Related U.S. Application Data

(60) Provisional application No. 62/328,554, filed on Apr. 27, 2016.

(51) Int. Cl.
*A61B 1/12* (2006.01)
*A61B 1/00* (2006.01)
(Continued)

(52) U.S. Cl.
CPC ............ *C09D 5/00* (2013.01); *A61B 1/00066* (2013.01); *A61B 1/00071* (2013.01);
(Continued)

(58) Field of Classification Search
CPC .. C09D 5/00; C09D 5/16; A61B 1/126; A61B 1/127; A61B 1/00071;
(Continued)

(56) References Cited

U.S. PATENT DOCUMENTS 10,391,506 B2 * 8/2019 Meuler .................... C09D 7/63
10,946,399 B2 * 3/2021 Meuler .................... C08K 5/02
(Continued)

FOREIGN PATENT DOCUMENTS

WO    WO-2012/100100 A2    7/2012
WO    WO-2013/106588 A1    7/2013
(Continued)

OTHER PUBLICATIONS

Anand et al., "Enhanced Condensation on Lubricant-Impregnated Nanotextured Surfaces" ACS Nano, vol. 6, No. 11, pp. 10122-10129, Oct. 2, 2012.
(Continued)

*Primary Examiner* — Anh T Nguyen
*Assistant Examiner* — Shankar Raj Ghimire
(74) *Attorney, Agent, or Firm* — Wilmer Cutler Pickering Hale and Dorr LLP

(57) ABSTRACT

A transparent repellent, liquid-infused coating applied onto the distal end of an endoscope that prevents vision loss and reduces fouling is described. Also described is a disposable endoscope window that is coated in a transparent, repellant,
(Continued)

Control endoscope          Endoscope modified
(unmodified )              with Liquid-infused
                           Coating Camera Working channel i          ii          iii          iv          v

PDMS liquid-infused coating for attachment to the distal end or distal window of an endoscope to obviate vision loss. Also described is an endoscope comprising a miniature camera coated in a transparent, repellent, liquid-infused coating.

24 Claims, 28 Drawing Sheets

(51) Int. Cl.

| | |
|---|---|
| *A61B 1/012* | (2006.01) |
| *A61B 1/018* | (2006.01) |
| *A61B 1/05* | (2006.01) |
| *A61B 1/07* | (2006.01) |
| *C09D 5/00* | (2006.01) |
| *C09D 5/16* | (2006.01) |
| *G02B 27/00* | (2006.01) |
| *A61B 1/31* | (2006.01) |

(52) U.S. Cl.
CPC ........ *A61B 1/00096* (2013.01); *A61B 1/0125* (2013.01); *A61B 1/018* (2013.01); *A61B 1/051* (2013.01); *A61B 1/07* (2013.01); *A61B 1/126* (2013.01); *A61B 1/127* (2013.01); *C09D 5/16* (2013.01); *G02B 27/0006* (2013.01); *A61B 1/31* (2013.01)

(58) Field of Classification Search
CPC ... A61B 1/00066; A61B 1/0125; A61B 1/018; A61B 1/051; A61B 1/07; A61B 1/00096; A61B 1/31; G02B 27/0006
See application file for complete search history.

(56) References Cited

U.S. PATENT DOCUMENTS

| | | | |
|---|---|---|---|
| 2003/0023143 A1* | 1/2003 | Abe ........................ A61B 1/005 | 600/153 |
| 2006/0068154 A1* | 3/2006 | Parce ................... C09D 11/037 | 428/76 |
| 2009/0306475 A1* | 12/2009 | Yamamoto ............... A61B 1/05 | 600/110 |
| 2010/0119774 A1* | 5/2010 | Ogawa ................. C09D 5/1612 | 427/337 |
| 2012/0209074 A1* | 8/2012 | Titus .................. A61B 1/00137 | 600/153 |
| 2013/0090527 A1* | 4/2013 | Axon ................. A61B 1/00075 | 600/114 |
| 2013/0172676 A1 | 7/2013 | Levy et al. | |
| 2013/0267778 A1* | 10/2013 | Rehe .................. A61B 1/00096 | 600/125 |
| 2013/0281779 A1 | 10/2013 | Robertson | |
| 2014/0147627 A1* | 5/2014 | Aizenberg .............. A61L 15/24 | 428/141 |
| 2014/0187666 A1 | 7/2014 | Aizenberg et al. | |
| 2014/0275787 A1* | 9/2014 | Miyamoto ............. A61B 1/126 | 600/139 |
| 2016/0025899 A1* | 1/2016 | Ishizeki ................... G02B 1/18 | 428/141 |
| 2016/0144079 A1* | 5/2016 | Ingber ..................... A61L 27/34 | 428/447 |
| 2016/0287058 A1* | 10/2016 | Ye ...................... A61B 1/00158 | |
| 2018/0127616 A1* | 5/2018 | Tuteja ................... C08G 18/61 | |

FOREIGN PATENT DOCUMENTS

| | | | |
|---|---|---|---|
| WO | WO-2014/012039 | 1/2014 | |
| WO | WO-2014/012079 | 1/2014 | |
| WO | WO-2014/012080 A1 | 1/2014 | |
| WO | WO-2014012039 A1 * | 1/2014 | .............. B05D 5/08 |

OTHER PUBLICATIONS

Barca et al., "Silicone Oil: Different Physical Proprieties and Clinical Applications," BioMed Research International, Jun. 11, 2014, vol. 2014, Article ID 502143, 7 pages.

Bessell et al., "Maintenance of a clear vision during laparoscopic surgery," Minimally Invasive Therapy & Allied Technologies (1996) published online Jul. 10, 2009, vol. 5, pp. 450-455.

Colt, "Bronchoalveolar Lavage," Journal of Bronchology, Apr. 1995, vol. 2, No. 2, 3 pages.

Davila et al., "Use and Application of Stem Cells in Toxicology." Toxicological Sciences, Mar. 10, 2004, vol. 79, No. 2, pp. 214-223.

Decher et al., "Buildup of ultrathin multilayer films by a self-assembly process: III. Consecutively alternating adsorption of anionic and cationic polyelectrolytes on charged surfaces," Thin Solid Films, Apr. 30, 1992, vol. 210-211, pp. 831-835.

Deng et al., (2012) "Candle Soot as a Template for a Transparent Robust Superamphiphobic Coating," Science, Jan. 6, 2012, vol. 335, No. 6064, pp. 67-70.

Donaldson et al., "Mucus Clearance and Lung Function in Cystic Fibrosis with Hypertonic Saline," New England Journal of Medicine, Jan. 19, 2006, vol. 354, No. 3, pp. 241-250.

Du Rand et al., "British Thoracic Society Guideline for Diagnostic Flexible Bronchoscopy in Adults," Thorax, first published Jul. 16, 2013, vol. 68, pp. i1-i44.

Du Rand et al., "British Thoracic Society Guidline for Advanced Diagnostic and Therapeutic Flexible Bronchoscopy in Adults," Thorax, first published Oct. 10, 2011, vol. 66, pp. iii1-iii21.

Eisler "Deadly bacteria on medical scopes trigger infections," USA Today, Jan. 21, 2015, 3 pages. (http://www.usatoday.com/story/news/2015/01/21/bacteria-deadly-endoscope-contamination/22119329/).

Epstein et al., "Liquid-infused structured surfaces with exceptional anti-biofouling performance," Proceedings of the National Academy of Sciences, Aug. 14, 2012, vol. 109, No. 33, pp. 13182-13187.

Flemming et al., "Principles determining optical clarity in endoscopic surgery," Minimally Invasive Therapy & Allied Technologies (1996) published online Jul. 10, 2009, vol. 5, pp. 440-444.

Griese, "Pulmonary surfactant in health and human lung diseases: state of the art," European Respiratory Journal, Jun. 1, 1999, vol. 13, No. 6, pp. 1455-1476.

Henderson et al., "Cystic fibrosis airway secretions exhibit mucin hyperconcentration and increased osmotic pressure," The Journal of Clinical Investigation, Jul. 2014, vol. 124, No. 7, pp. 3047-3060.

Hiller et al., "Reversibly erasable nanoporous anti-reflection coatings from polyelectrolyte multilayers," Nature Materials, Sep. 2, 2002, vol. 1, No. 1, pp. 59-63.

Howell et al., "Self-Replenishing Vascularized Fouling-Release Surfaces," ACS Applied Materials & Interfaces, Jul. 9, 2014, vol. 6, No. 15, pp. 13299-13307.

Howell et al., "Stability of Surface-Immobilized Lubricant Interfaces under Flow," Chemistry of Materials, Feb. 4, 2015, vol. 27, No. 5, pp. 1792-1800.

International Search Report and Written Opinion mailed Sep. 15, 2017, in the International Application No. PCT/US17/29858, 16 pages.

ISO 10993-5, "Biological Evaluation of Medical Devices—Part 5: Tests for In Vitro Cytotoxicity," International Organization for Standardization, Third Edition Jun. 1, 2009, 42 pages.

Kim et al., "Hierarchical or not? Effect of the length scale and hierarchy of the surface roughness on omniphobicity of lubricant-infused substrates," Nano Letters, Mar. 6, 2013, vol. 13, No. 4, pp. 1793-1799.

Krogman et al., "Spraying asymmetry into functional membranes layer-by-layer," Nature Materials, Jun. 2009, vol. 8, No. 6, pp. 512-518.

Lafuma et al., "Slippery pre-suffused surfaces," EPL, Dec. 2011, vol. 96, No. 5, 5 pages.

Lawrentschuk et al., "Laparoscopic Lens Fogging: A Review of Etiology and Methods to Maintain a Clear Visual Field," Journal of Endourology, Jun. 2010, vol. 24, No. 6, pp. 905-913.

(56) References Cited

OTHER PUBLICATIONS

Leffler et al., "The Incidence and Cost of Unexpected Hospital Use After Scheduled Outpatient Endoscopy," Arch Intern Med, Oct. 25, 2010, vol. 170, No. 19, pp. 1752-1757.

Leslie et al., "A bioinspired omniphobic surface coating on medical devices prevents thrombosis and biofouling," Nature Biotechnology, Nov. 2014, vol. 32, No. 11, pp. 1134-1140.

Li et al. "Hydrophobic Liquid-Infused Porous Polymer Surfaces for Antibacterial Applications," ACS Applied Materials & Interfaces, Jun. 18, 2013, vol. 5, No. 14, pp. 6704-6711.

MacCallum et al., "Liquid-Infused Silicone as a Biofouling-Free Medical Material," ACS Biomaterials Science & Engineering, Dec. 4, 2014, vol. 1, No. 1, pp. 43-51.

Macklem, "The Physiology of Small Airways," American Journal of Respiratory and Critical Care Medicine, May 1, 1998, vol. 157, pp. S181-S183.

Manabe et al., "Biocompatible Slippery Fluid-Infused Films Composed of Chitosan and Alginate via Layer-by-Layer Self-Assembly and Their Antithrombogenicity," ACS Applied Materials & Interfaces, Feb. 3, 2015, vol. 7, No. 8, pp. 4763-4771.

Marquez-Martín et al., "Endobronchial Administration of Tranexamic Acid for Controlling Pulmonary Bleeding: A Pilot Study," Journal of Bronchology and Interventional Pulmonology, Apr. 2010, vol. 17, No. 2, pp. 122-125.

Ohdaira et al., "Antifogging effects of a socket-type device with the superhydrophilic, titanium dioxide-coated glass for the laparoscope," Surgical Endoscopy, published online Dec. 13, 2006, vol. 21, pp. 333-338.

Rogers et al., "The porcine lung as a potential model for cystic fibrosis," American Journal of Physiology, Lung Cellular and Molecular Physiology, Aug. 2008 (published online May 16, 2008), vol. 295, No. 2, 59 pages.

Singh et al., (2009) "Endoscopy. Quality and Utilization Implications of a Novel Colonoscopic Metric: Post Polypectomy Interval Repeat Ratios," The American Journal of Gastroenterology, vol. 104, Oct. 2009, 1 page.

Sunny et al., "Lubricant-Infused Nanoparticulate Coatings Assembled by Layer-by-Layer Deposition," Advanced Functional Materials, Sep. 1, 2014, vol. 24, Issue 42, pp. 6658-6667.

Tuteja, Anish, et al., "Robust omniphobic surfaces," PNAS, Nov. 25, 2008, vol. 105, No. 47, pp. 18200-18205.

UCLA Health, "UCLA statement on notification of patients regarding endoscopic procedures," Mar. 10, 2015, 8 pages. (https://www.uclahealth.org/news/ucla-statement-on-notification-of-patients-regarding-endoscopic-procedures).

Vogel et al., "Transparency and damage tolerance of patternable omniphobic lubricated surfaces based on inverse colloidal monolayers," Nature Communications, Jul. 31, 2013, 4:2167, 10 pages.

Wong et al., "Bioinspired self-repairing slippery surfaces with pressure-stable omniphobicity," Nature, Sep. 22, 2011, vol. 477, No. 7365, pp. 443-447.

Yuan et al., "Facile Fabrication of Lubricant-Infused Wrinkling Surface for Preventing Thrombus Formation and Infection," ACS Applied Materials & Interfaces, Aug. 13, 2015, vol. 7, pp. 19466-19473.

Kim et al., "Hydroglyphics: Demonstration of Selective Wetting on Hydrophilic and Hydrophobic Surface," Journal of Chemical Education (2013), Nov. 8, 2012, vol. 90, pp. 625-628.

Kim et al., "Liquid-Infused Nanostructured Surfaces with Extreme Anti-Ice and Anti-Frost Performance," ACS Nano, published online Jun. 10, 2012, vol. 6(8), pp. 6569-6577.

Wang et al., "Secrets revealed—Spatially selective wetting of plasma-patterned periodic mesoporous organosilica," Can. J. Chem., published online Nov. 21, 2012, vol. 90, pp. 1063-1068.

Wilson et al., "Inhibition of ice nucleation by slippery liquid-infused porous surfaces (SLIPS)," Phys. Chem. Chem. Phys. (2013), Nov. 14, 2012, vol. 15, pp. 581-585.

Yao et al., "Fluorogel Elastomers with Tunable Transparency, Elasticity, Shape-Memory, and Antifouling Properties," Angewandte Chemie International Edition, published online Mar. 18, 2014, vol. 53, pp. 4418-4422.

\* cited by examiner b a

ANTI-FOULING ENDOSCOPES AND USES THEREOF

CROSS REFERENCE TO RELATED APPLICATION

This application is a U.S. National Stage application under 35 U.S.C. § 371 of International Patent Application No. PCT/US2017/029858, filed Apr. 27, 2017, which claims the benefit of U.S. Provisional Application No. 62/328,554, filed Apr. 27, 2016, the contents of which are hereby incorporated by reference.

COPYRIGHT NOTICE

INCORPORATION BY REFERENCE

All patents, patent applications and publications cited herein are hereby incorporated by reference in their entirety in order to more fully describe the state of the art as known to those skilled therein as of the date of the invention described herein.

FIELD OF THE INVENTION

The present application relates to anti-fouling materials. More particularly, the present application relates to improving the visual field of endoscopes by utilizing anti-fouling materials.

BACKGROUND

Camera-guided instruments have become an integral component of modern technologies with the use of these instruments ranging from oil field exploration, sanitation inspections, marine exploration, to robotics. Their operation is heavily compromised in highly contaminating environments where oil, sewage, marine fouling etc. can disrupt the visual field. Periodically cleaning the surfaces of these cameras for their continued effective function requires costly and time consuming methods. There is a clear need for an antifouling, transparent material that can be applied to the surface of a lens or lens window to obviate this vision loss. Perhaps most significantly and more than in any industry or application, these challenges manifest in medical procedures such as endoscopy.

Endoscope operators use the device to inspect interior regions of the human body and, in the case of flexible endoscopes, obtain samples for diagnostic studies and provide minimally invasive therapy via instruments passed through the working channel. All these procedures bring the camera lens or lens window in close contact with body fluids, which adsorb onto the lens or lens window and compromise the visual field, risking imprecise or undesired movements of the device that damage the surrounding tissue and harm the patient. Traditionally, the lens or lens window is cleared via suction, vigorous saline irrigation, or gentle rubbing against the tissue walls. Often, the endoscope needs to be retracted and manually cleaned, which is more likely to occur during the most crucial points in a procedure, for example during excessive blood flow caused by a biopsy. Rigid endoscopes do not have a working channel, so rubbing or withdrawal to wipe clean are the only recourses. All these measures impose risks to the patient's health. Of particular concern are procedures in flexible bronchoscopy where wiping against the delicate tissue in the lungs can cause lens or lens window re-occlusion and coughing reflexes, long periods of suction in narrow airways can lead to luminal collapse, and saline irrigation can dislodge previously formed clots leading to undesired bleeding. Retracting the endoscope and wiping it clean results in periodic, highly undesired interruptions contributing to longer and potentially riskier procedures. Conversion to open surgery may even be required when complications arise from procedures performed while visually impaired.

Traditional superhydrophobic surfaces fail when exposed to biological elements, such as proteins, cells, bacteria, and the formation of blood clots. The last decade has witnessed significant development in the design of Lotus leaf-inspired superamphiphobic surfaces, which show repellency of various liquids. Recently, liquid-infused coatings, consisting of a porous structure infiltrated with a liquid, have emerged as an alternative strategy for repellent materials (Wong T-S, et al. (2011) Bioinspired self-repairing slippery surfaces with pressure-stable omniphobicity. *Nature* 477(7365):443-447).

There exists a need for an antifouling, transparent material that can be applied to the surface of endoscope lens or lens windows to obviate vision loss.

SUMMARY OF THE INVENTION

A self-cleaning, biocompatible, transparent coating on endoscopes is described. A liquid-infused coating is used to create transparent slippery coatings that prevent adhesion of biological fluids, while maintaining optical transparency to permit camera imaging.

The present invention provides an endoscope that exhibits a combination of critical, but difficult to achieve properties. In addition to satisfying the general requirements for coatings of medical devices (e.g., to be conformal, mechanically robust, biocompatible, and anti-microbial), it additionally displays high transparency and extreme resistance to fouling by body fluids that allows the maintenance of a clear visual field throughout the procedure when contacting biological fluids. The endoscope described herein sustains repellency throughout an endoscopic procedure while in direct contact with proteins, cells, and bacteria as well as during the formation of blood clots. In one or more embodiments, the endoscopic lens or lens window maintains its transparency throughout the procedure.

It is understood that any of the embodiments described below can be combined in any desired way, and that any embodiment or combination of embodiments can be applied to each of the aspects described below, unless the context indicates otherwise.

In one aspect, the present invention provides an endoscope, comprising: an insertion tube and a proximal body, the insertion tube starting from the proximal body and having a distal end with an objective lens for imaging, and the proximal body housing one or more control knobs for rotating and angulating the distal end of the insertion tube; a fiber optic system to conduct light from a source through the proximal body to the distal end of the insertion tube; wherein the distal end comprises a lubricating fluid layer, wherein the lubricating fluid is immiscible with a biological material, the lubricating layer forming an ultra-smooth surface over a solid substrate, wherein the lubricating fluid adheres to the substrate and the substrate is preferentially wetted by the lubricating fluid; and wherein the solid substrate and lubricating fluid forming a slippery surface is optically transparent.

In some embodiments, the proximal body comprises an eyepiece for viewing.

In some embodiments, the invention further comprises a second fiber optic system to transport images as reflected light from the distal end of the insertion tube to the eyepiece.

In some embodiments, the invention further comprises a CMOS or CCD chip, and a wire system, to transmit electrical image data from the distal end of the insertion tube through the proximal body to an external video processing unit.

In some embodiments, the proximal body further houses a first plumbing control and a first outlet for a first plumbing system, wherein the first plumbing system comprises a channel running through the endoscope from the proximal body to the distal end of the insertion tube.

In some embodiments, the proximal body further houses a second plumbing control and a second outlet for a second plumbing system, wherein the second plumbing system comprises a second channel running through the endoscope from the proximal body to the distal end of the insertion tube.

In some embodiments, the proximal body further houses a third plumbing control and a third outlet for a third plumbing system, wherein the third plumbing system comprises a third channel running through the endoscope from the proximal body to the distal end of the insertion tube.

In some embodiments, the proximal body further houses a first port for access to a first working channel, wherein the first working channel runs through the endoscope from the port of the proximal body to the distal end of the insertion tube.

In some embodiments, the proximal body further houses a second port for access to a second working channel, wherein the second working channel runs through the endoscope from the second port of the proximal body to the distal end of the insertion tube.

In some embodiments, the first, second, or third plumbing system is selected from the group consisting of an irrigation system, a suction system, and an insufflation system.

In some embodiments, the first or second working channel is used to introduce a camera, forceps, a cytology brush, one or more biopsy instruments, and combinations thereof.

In some embodiments, the camera is used for visual inspection. In some embodiments, the entirety of the endoscope including a camera capturing and transmitting images wirelessly, is housed inside a pill or capsule. The pill or capsule may be swallowed by the patient or otherwise introduced to the patient. In some embodiments, the system comprises an extendable scope-within-scope. In accordance with this aspect, the parent scope incorporates a separate, extended reach secondary or auxiliary scope. The insertion tube of the secondary scope tool is received in a tool channel of the parent scope, and is 'extended reach' in that the secondary insertion tube is extendable from the tip of the primary insertion tube of the parent scope an additional distance beyond the reach of the primary scope tube.

In some embodiments, the one or more biopsy instruments is used to perform a biopsy.

In some embodiments, the solid substrate is porous.

In some embodiments, the solid substrate is a polymer infiltrated with lubricating liquid.

In some embodiments, the solid substrate is smooth and functionalized to hold the lubricating fluid.

In some embodiments, the solid substrate is integral with the lens.

In some embodiments, the solid substrate is disposable and not integral to the lens.

In some embodiments, the distal end further comprises a distal window.

In some embodiments, the solid substrate is integral with the distal window.

In some embodiments, the solid substrate is secured to the distal window.

In some embodiments, the solid substrate is secured to the distal window using an optically transparent adhesive.

In some embodiments, the solid substrate is configured to cover an entire surface of the distal end of the endoscope.

In some embodiments, the solid substrate is configured to cover a portion of the distal end of the endoscope.

In some embodiments, the optically transparent adhesive comprises poly(dimethylsiloxane).

In some embodiments, the lens comprises glass, sapphire, or a transparent polymer.

In some embodiments, the distal window comprises glass, sapphire, or a transparent polymer.

In some embodiments, the substrate is a porous surface comprising glass, sapphire, or a transparent polymer.

In some embodiments, the substrate comprises silica nanoparticles or other inorganic oxide nanoparticles. In some embodiments, the nanoparticles include nanoparticles made of metal oxides, mixed metal oxides, and/or metal sulfide nanoparticles; some particular examples include vanadia, silica, alumina, noble metal oxides, platinum group metal oxides, titania, zirconia, hafnia, molybdenum oxides, tungsten oxides, rhenium oxides, tantalum oxide, niobium oxide, chromium oxides, scandium, yttrium, lanthanum, thorium, uranium oxides, other rare earth oxides, or a combination thereof.

In some embodiments, the substrate is functionalized with a partially or fully fluorinated alkyl chain using chlorosilane coupling, amide coupling, or glicydyl chemistry. Polymerized $C_4F_8$ can also be deposited on substrates using a reactive ion etching chamber.

In some embodiments, the partially or fully fluorinated alkylsilane is a (1H,1H,2H,2H-tridecafluorooctyl)-trichlorosilane, which is reactive with the surface of the substrate.

In some embodiments, the substrate is functionalized with a hydrocarbon group. In some embodiments, the hydrocarbon group is linear, branched or a combination thereof.

In some embodiments, the hydrocarbon group is decyl or dodecyl.

In some embodiments, the lubricating fluid is selected from the group consisting of silicone oil, mineral oil, food-grade oil, partially or fully fluorinated oils, and combinations thereof.

In some embodiments, the lubricating fluid is a perfluoropolyether.

In some embodiments, the lubricating fluid is perfluoroperhydrophenanthrene, perfluorodecalin or other fluorinated fluids (including but not limiting to the tertiary perfluoroalkylamines (such as perfluorotri-n-pentylamine, FC-70 by 3M, perfluorotri-n-butylamine FC-40, etc), perfluoroalkylsulfides and perfluoroaikylsulfoxides, perfluoroalkylemers, perfluorocycloethers (like FC-77) and perfluoropolyethers (such as KRYTOX family of lubricants by DuPont), perfluoroalkylphosphines and perfluoroalkylphosphmeoxides as well as their mixtures can be used for these applications); polydimethylsiloxane and their functional modifications; food compatible liquids. Examples of food compatible liquids include, but are not limiting to, olive oil, canola oil, coconut oil, corn oil, rice bran oil, cottonseed oil, grape seed oil, hemp oil, mustard oil, palm oil, peanut oil, pumpkin seed oil, safflower oil, sesame oil, soybean oil, sunflower oil, tea seed oil, walnut oil, and mixtures of any of the above oils.

In some embodiments, the lubricating fluid comprises silicone oils of different viscosities.

In some embodiments, the solid substrate is reversibly secured to the distal window. In some embodiments, the solid substrate is reversibly secured to the distal window using a screw-on attachment or a clip-on attachment.

In some embodiments, the invention provides an endoscope for use in medical procedures. In some embodiments, the invention provides an endoscope for use in veterinary applications.

In some embodiments, the invention provides an endoscope for use in sanitation inspection.

In some embodiments, the invention provides an endoscope for use in robotic devices.

In some embodiments, the invention provides an endoscope for use in oil exploration.

In another aspect, the invention provides an optically transparent article for attaching to the distal end or distal window of an insertion tube of an endoscope, comprising: a lubricating fluid layer, wherein the lubricating fluid is immiscible with a biological material, the lubricating layer forming an ultra-smooth surface over a solid substrate, wherein the lubricating fluid adheres to the substrate and the substrate is preferentially wetted by the lubricating fluid; and wherein the solid substrate and lubricating fluid forming a slippery surface is optically transparent, and wherein the solid substrate is configured to be secured over a viewing window of an endoscope or is integral with the lens.

In some embodiments, the solid substrate is porous.

In some embodiments, the solid substrate is a polymer infiltrated with lubricating liquid resulting in an over-layer of lubricant that results in antifouling performance.

In some embodiments, the solid substrate is smooth and functionalized to hold the lubricating fluid.

In some embodiments, the solid substrate is configurable for securing to an endoscope using an adhesive.

In some embodiments, the substrate is a porous surface comprising glass, sapphire, or a transparent polymer.

In some embodiments, the substrate comprises silica nanoparticles or other inorganic oxide nanoparticles.

In some embodiments, the substrate is functionalized with a partially or fully fluorinated alkyl chain using chlorosilane coupling, amide coupling, or glicydyl chemistry which is reactive with the surface of the substrate. Polymerized $C_4F_8$ can also be deposited on substrates using a reactive ion etching chamber.

In some embodiments, the partially or fully fluorinated alkylsilane is a (1H,1H,2H,2H-tridecafluorooctyl)-trichlorosilane.

In some embodiments, the substrate is functionalized with a hydrocarbon group.

In some embodiments, the hydrocarbon groups are linear, branched or combinations thereof.

In some embodiments, the lubricating fluid is selected from the group consisting of silicone oil, mineral oil, food-grade oil, partially or fully fluorinated oils, and combinations thereof.

In some embodiments, the lubricating fluid is a perfluoropolyether.

In some embodiments, the lubricating fluid is perfluoroperhydrophenanthrene, perfluorodecalin or other fluorinated fluids (including but not limiting to the tertiary perfluoroalkylarnines (such as perfluorotri-n-pentylamine, FC-70 by 3M, perfluorotri-n-butylamine FC-40, etc), perfluoroalkylsulfides and perfluoroaikylsulfoxides, perfluoroalkylemers, perfluorocycloethers (like FC-77) and perfluoropolyethers (such as KRYTOX family of lubricants by DuPont), perfluoroalkylphosphines and perfluoroalkylphosphmeoxides as well as their mixtures can be used for these applications); polydimethylsiloxane and their functional modifications; food compatible liquids (including but not limiting to olive oil, canola oil, coconut oil, corn oil, rice bran oil, cottonseed oil, grape seed oil, hemp oil, mustard oil, palm oil, peanut oil, pumpkin seed oil, safflower oil, sesame oil, soybean oil, sunflower oil, tea seed oil, walnut oil, and a mixtures of any of the above oils).

In some embodiments, the lubricating fluid comprises silicone oils of different viscosities.

In some embodiments, the article is a cap.

In some embodiments, the article is a sheath.

In another aspect, the invention provides an endoscope comprising: an insertion tube and a proximal body, the insertion tube starting from the proximal body and having a distal end with an objective lens for imaging, and the proximal body housing one or more control knobs for rotating and angulating the distal end of the insertion tube, and a port for access to a first working channel, wherein the first working channel runs through the endoscope from the port of the proximal body to the distal end of the insertion tube; a fiber optic system to conduct light from a source through the proximal body to the distal end of the insertion tube; a camera comprising a CMOS or a CCD chip, a camera body, and a camera cable, the camera body having a distal end with a second objective lens for imaging and a proximal end integrated with the camera cable; wherein the camera cable comprises a wire system to transmit electrical image data from the camera body to an external video processing unit, wherein the second objective lens comprises a lubricating fluid layer, wherein the lubricating fluid is immiscible with a biological material, the lubricating layer forming an ultra-smooth surface over a solid substrate; wherein the lubricating fluid adheres to the substrate and the substrate is preferentially wetted by the lubricating fluid; wherein the solid substrate and lubricating fluid forming a slippery surface is optically transparent; and wherein said camera is housed within the first working channel and reversibly extends from the first working channel at the distal end of the insertion tube.

In some embodiments, the camera further comprises a fiber optic light source.

In some embodiments, the camera comprises multiple lenses.

In some embodiments, the proximal body further houses a plumbing control and an outlet for a plumbing system, wherein the plumbing system comprises a channel running through the endoscope from the proximal body to the distal end of the insertion tube.

In some embodiments, the proximal body further houses a second port for access to a second working channel, wherein the second working channel runs through the endoscope from the second port of the proximal body to the distal end of the insertion tube.

In some embodiments, the first or second working channel is used to introduce forceps, a cytology brush, one or more biopsy instruments, and combinations thereof.

In some embodiments, the camera body comprises a lubricating fluid layer, wherein the lubricating fluid is immiscible with a biological material, the lubricating layer forming an ultra-smooth surface over a solid substrate;

wherein the lubricating fluid adheres to the substrate and the substrate is preferentially wetted by the lubricating fluid; wherein the solid substrate and lubricating fluid forming a slippery surface is optically transparent.

In some embodiments, the camera has a diameter less than 2 mm.

In some embodiments, the substrate is a porous surface comprising glass, sapphire, or a transparent polymer.

In some embodiments, the substrate comprises silica nanoparticles or other inorganic oxide nanoparticles.

In some embodiments, the substrate is functionalized with a partially or fully fluorinated alkyl chain using chlorosilane coupling, amide coupling, or glicydyl chemistry which is reactive with the surface of the substrate. Polymerized $C_4F_8$ can also be deposited on substrates using a reactive ion etching chamber.

In some embodiments, the partially or fully fluorinated alkylsilane is a (1H,1H,2H,2H-tridecafluorooctyl)-trichlorosilane.

In some embodiments, wherein the substrate is functionalized with a hydrocarbon group.

In some embodiments, the hydrocarbon group is linear, branched or combinations thereof. In some embodiments, the hydrocarbon group is nonyl, decyl, undecyl or dodecyl.

In some embodiments, the lubricating fluid is selected from the group consisting of silicone oil, mineral oil, food-grade oil, partially or fully fluorinated oils, and combinations thereof.

In some embodiments, the lubricating fluid is a perfluoropolyether.

In some embodiments, the lubricating fluid is perfluoroperhydrophenanthrene or perfluorodecalin.

In some embodiments, the lubricating fluid comprises silicone oils of different viscosities.

In some embodiments, the invention provides an endoscope for use in medical procedures.

In some embodiments, the invention provides an endoscope for use in sanitation inspection.

In some embodiments, the invention provides an endoscope for use in robotic devices.

In some embodiments, the invention provides an endoscope for use in oil exploration.

In some embodiments, the invention provides a capsule endoscope comprising a capsule body and a camera disposed inside the capsule body, wherein the capsule body includes a viewing window and the camera includes a lens. The endoscope further includes a lubricating fluid layer, wherein the lubricating fluid is immiscible with a biological material, the lubricating layer forming an ultra-smooth surface over a solid substrate, wherein the lubricating fluid adheres to the substrate and the substrate is preferentially wetted by the lubricating fluid, and wherein the solid substrate and lubricating fluid forming a slippery surface is optically transparent, and wherein the solid substrate is configured to be secured over the viewing window or is integral with the lens.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

(FIGS. 1C-1D) An endoscope is modified with a disposable coated glass coverslip (FIG. 1C(i)). A 6 mm glass coverslip is cut by a diamond scribe in the shape of a crescent to fit over the distal end of the endoscope to cover the lens while leaving the working channel exposed. This coverslip is coated with a layer-by-layer based nanoscale surface coating as previously described and infused with a lubricant to facilitate repellency (FIG. 1C(ii)). A drop of polydimethylsiloxane (PDMS) is added to the surface of the distal end of the scope (FIG. 1C(iii)) prior to fixing the coated glass on the endoscope lens (FIG. 1C(iv)). The PDMS is cured, thereby securing the coverslip to the surface of the lens (FIG. 1C(v)) while exposing the working channel. (FIG. 1D) The distal end of the insertion tube of an endoscope is modified by attaching or affixing a disposable coated glass coverslip.

(FIG. 3B) The uncoated endoscope fails immediately after one dip while the 10 cSt oil allows for repellency up to 100 dips with no fouling. Submersions in whole porcine blood was also performed using endoscopes coated with (FIG. 3C) 350 cSt, and (FIG. 3D) 500 cSt silicone oil. The droplets of blood on the 350 cSt and 500 cSt silicone oil surfaces do not shed as quickly from the surface and pool before they are large enough to be shed from the surface. This contributes to the oscillatory behavior in visibility.

(FIG. 4B) While plain glass fails immediately after one dip, endoscopes coated with the 10 cSt silicone oil (Coating Replicate 2 is used as an example) remains clear at the $8^{th}$ dip. (FIG. 4C) 350 cSt silicone oil also shows an oscillatory behavior in clearance.

(FIG. 5A) Mouse mesenchymal stem cells were grown in tissue culture wells and treated with varying concentrations of 20 nm silica particles and stained for live/dead cells. As an estimation of the worst-case scenario, the concentration of nanoparticles dissolved in 1 mL of solution was calculated assuming all particles of the coating are released from the coating. This concentration was determined to be $6.7 \times 10^{-4}$ wt. % (falling between 0-0.003 wt. % indicated by the dashed box in FIG. 5C) (calculation shown in Example 1). (FIG. 5B) The cells were grown on plain glass and the silicone oil-infused coating and stained for live/dead cells. There are no visible dead cells on the control and the coating. (FIG. 5C) Quantification of area coverage with live (black) and dead (red) cells. In the concentration regime of interest and even at the concentration that exceeds the region of interest by more than an order of magnitude, no toxicity is detected and coverage remains equal to the control. (FIG. 5D) Similar quantification is also performed for cells grown on plain glass surfaces versus liquid-infused surfaces. The number of dead cells is negligible on the coating as well as the plain glass control.

(FIG. 6A) Contact of the endoscope with the lung secretions in an ex vivo lung. (FIG. 6B) Endobronchial biopsies using an uncoated bronchoscope were performed in the right lung of a porcine lung while the liquid-infused coated bronchoscope sampled the left lung. R refers to rubbing against airway walls and S refers to suction for the methods used for clearance. The symbol * next to biopsy 2 and 3 on the control images for "time to clear" indicates that complete clearance is not achieved. The control endoscope fouls for all three biopsies with extensive suction and rubbing required for biopsy 2 where complete visibility is not regained. The average time for clearance for all three procedures is 67 seconds. The liquid-infused coating does not foul after the first biopsy and is quickly cleared using either suction or rubbing after the $2^{nd}$ and $3^{rd}$ biopsy with an average clearance time of 4 seconds. (FIG. 6C) Images obtained after performing a wedge (i.e., where the distal end is used to block the bleeding site and stop blood flow). Visualization is entirely retained after two submersions in blood (FIG. 6C(i)) and partially obstructed (~50% of clear field remained) after performing a 20 s blood suction and a three minute wedge (FIG. 6C(ii)).

(FIG. 9A) Dipping was performed in whole porcine blood using scopes coated with VITREON (8 cSt), PFPE (80 cSt) and PFPE (550 cSt). (FIG. 9B) The uncoated scope fails immediately after one dip while PFPE (80 cSt) oil allows for repellency up to 12 dips before failure. (FIG. 9C) Re-lubricating the endoscope prolongs the performance for 3 dips in blood before complete failure.

(FIG. 11A) Performance of silicone oil coatings in blood dipping experiments after submersions in 17 wt.-% mucin solution. The 10 cSt silicone oil coating fails after 13 dips while the 1:1 volume ratio of 10 cSt to 350 cSt silicone oil provides a clear image even after 50 dips. (FIG. 11B) Evaluating the repellency properties of a 1:1 ratio of 10 cSt and 350 cSt silicone oil coating in whole porcine blood with three replicates. A combined repellency effect of whole blood is achieved where the droplets are highly mobile on the surface as seen in the 10 cSt data while maximizing the potential longevity from the 350 cSt oil.

DETAILED DESCRIPTION

Figures 1A, 1B, 1C:
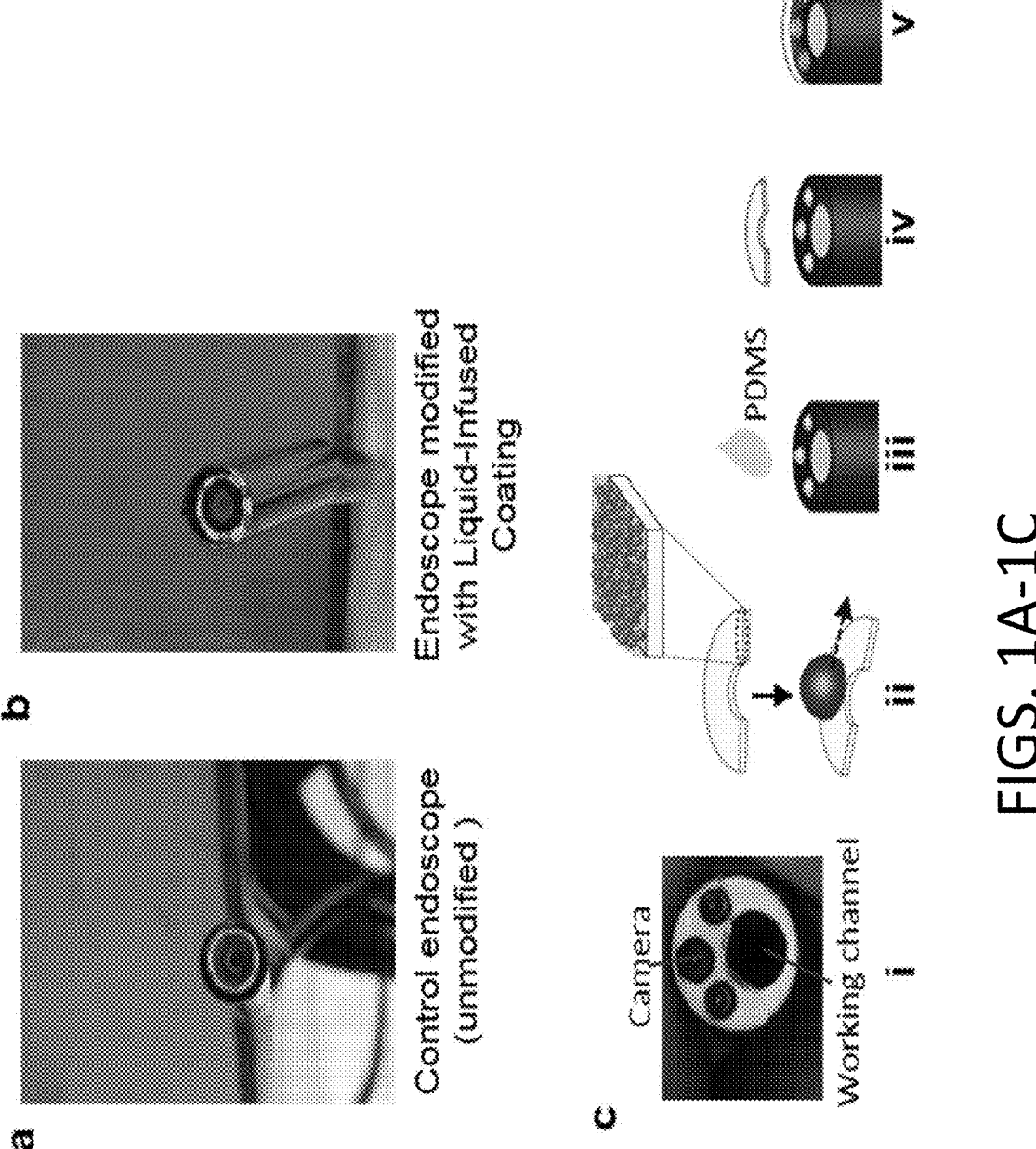
FIGS. 1A-1D show schematic of endoscope coating process. The unmodified (FIG. 1A) and the modified (FIG. 1B) pipe inspection camera used in the in vitro blood and mucus dipping experiments and the ex vivo experiment with lung surfactant.

Disclosed herein is an endoscope having a transparent, repellent, liquid-infused coating applied onto the distal end of an endoscope that prevents vision loss and reduces fouling. Also disclosed herein is a disposable endoscope window that is coated in a transparent, repellant, liquid-infused coating for permanent or removable attachment to the distal end or distal window of an endoscope to obviate vision loss. Also disclosed herein is an endoscope comprising a miniature camera coated in a transparent, repellent, liquid-infused coating, wherein the miniature camera extends from a working channel of the endoscope.

A traditional endoscope comprises an airtight and waterproof elongated tube having a distal end with an objective lens for imaging and a proximal end with an eyepiece for viewing. The tube can be rigid or flexible. An endoscope typically includes light transmitting pathways. The first pathway carries light into the body cavity and a return light pathway carries the image of the body cavity back to the viewer. Endoscopes may also include a camera or video recorder to document images observed by the viewer. Endoscopes can also include a separate port to allow for administration of drugs, suction, and irrigation, or introduction of instruments specific to the medical procedure.

In a typical rod lens endoscope, the distal end terminates with a transparent distal window. The distal window provides the primary seal at the distal end of the endoscope and protects the objective lens assembly. The distal window typically comprises optical glass. Distal windows may also comprise synthetic sapphire, which is a hard material that may be more durable and scratch resistant than conventional optical glass.

Flexible endoscopes provide access to various anatomical structures of the human body that cannot be reached by rigid endoscopes (e.g., gastrointestinal tract, respiratory tract) and allow for minimally invasive investigation of symptoms, diagnosis of pathology and application of directed therapies. Flexible endoscopes are completely watertight and generally comprise a proximal body, a flexible insertion tube, and an umbilical cord connecting the proximal body to a light source. The proximal body is designed to be held in one hand and typically includes the eyepiece. The proximal body houses the outlets for the plumbing systems, ports for access to the working channel(s), and the control knobs which allow rotation and angulation of the distal tip of the flexible insertion tube via a complex angulation system. The working channel, sometimes called an instrument channel, is hollow and provides aspiration possibilities and guides thin long instruments to, e.g., acquire specimen during the procedure. Working channels can be used for suction and for insertion of accessory instruments such as biopsy needles, forceps, cytology brushes. A fiber optic bundle conducts light from the light source through the scope to the distal end of the flexible insertion tube for field illumination through illuminations lens. A separate fiber optic bundle transports images as reflected light from the distal tip, which comprises a viewing aperture or objective lens, to the eyepiece. The objective lens can comprise optical glass or sapphire. The objective lens controls the visual range and determines the line of sight. The objective lens can be oriented at various degrees. The objective lens has two surfaces through which light passes and can be curved (concave or convex) or planar.

In video-based flexible endoscopes, the eyepiece and image fiber bundle are unnecessary. The use of a CCD (charge-coupled device) chip, together with an objective lens, allows for the transmission of electrical image data through the endoscope to an external video processing unit. The CCD chip is mounted behind a lens system at the distal end of the flexible insertion tube. Alternatively, a CMOS (complimentary metal-oxide semiconductor) chip can be used to transmit images electronically.

In one aspect, the lens or lens window at the distal tip of the insertion tube of an endoscope is coated in a transparent, repellent, liquid-infused coating. A transparent, repellent, oil-infused coating applied onto the lens or lens window at the distal end of the insertion tube of an endoscope provides a repellant surface that improves visual field and reduces fouling. The lens or lens window at the distal end comprises or is modified to comprise a roughened or porous surface layer that is optically transparent and light transmissive. In some embodiments, the surface structure of the roughened or porous surface layer comprises feature sizes that are under the diffraction limit. In some embodiments, the surface structure of the roughened or porous surface layer comprises feature sizes that are under 1 μm. The porous surface layer is a substrate for infiltration with a low surface energy liquid. Infusion of the substrate with a lubricating liquid, which is locked in place by its affinity for the substrate and/or capillary forces, creates an ultra-smooth surface containing partial or full liquid overlayer that is slippery and resists or reduces adhesion by particles and immiscible liquids. The ultra-smooth surface is a stable, defect-free, inert "slippery" interface is capable of repelling complex fluids, gases, and molecules or particulates contained within liquids of varying surface tensions. Liquids that can be repelled include biological liquids, both pure liquids and complex fluids, such as whole blood flow, mucus, and other secretions (some examples include plasma, serum, sweat, feces, urine, saliva, vaginal fluid, prostatic fluid, gingival fluid, amniotic fluid, intraocular fluid, cerebrospinal fluid, seminal fluid, sputum, ascites fluid, pus, nasopharengal fluid, wound exudate fluid, aqueous humour, vitreous humour, bile, cerumen, endolymph, perilymph, gastric juice, peritoneal fluid, pleural fluid, sebum, vomit, and combinations thereof). Solids like bacteria, proteins, and the like can also be repelled by the surface. In addition, natural and synthetic solutions such as those used in medicines, intravenous solutions, pharmaceutical manufacturing, and medication delivery systems can be repelled by the surface. Moreover, the repellant, oil-infused coating is chemically-inert, biocompatible, and non-toxic. Detail on the principles of slippery liquid infused layers is found in US Published Application No. 2014/0187666, which is incorporated herein in its entirety by reference.

In one aspect, the transparent, repellent, oil-infused coating coats an optically transparent, disposable endoscope attachment for attachment to the distal end of the insertion tube of an endoscope. In certain embodiments, the transparent, repellent, oil-infused coating coats an optically transparent, disposable cap for attachment to the distal end of the insertion tube of an endoscope. The cap can be attached or secured in any suitable manner. In certain embodiments, the cap is clipped on. In certain embodiments, the cap is screwed on. The cap can have openings of varying shapes and sizes. In certain embodiments, the transparent, repellent, oil-infused coating coats an optically transparent, disposable sheath for attachment to the distal end of the insertion tube of an endoscope. The length of the sheath may be any length compatible with the endoscope. In certain embodiments, the sheath covers the entire length of the insertion tube. In certain embodiments, the sheath partially covers the insertion tube. In certain embodiments, the sheath is flexible. In certain embodiments, the sheath conforms to the shape of the endoscope.

Figure 1D:
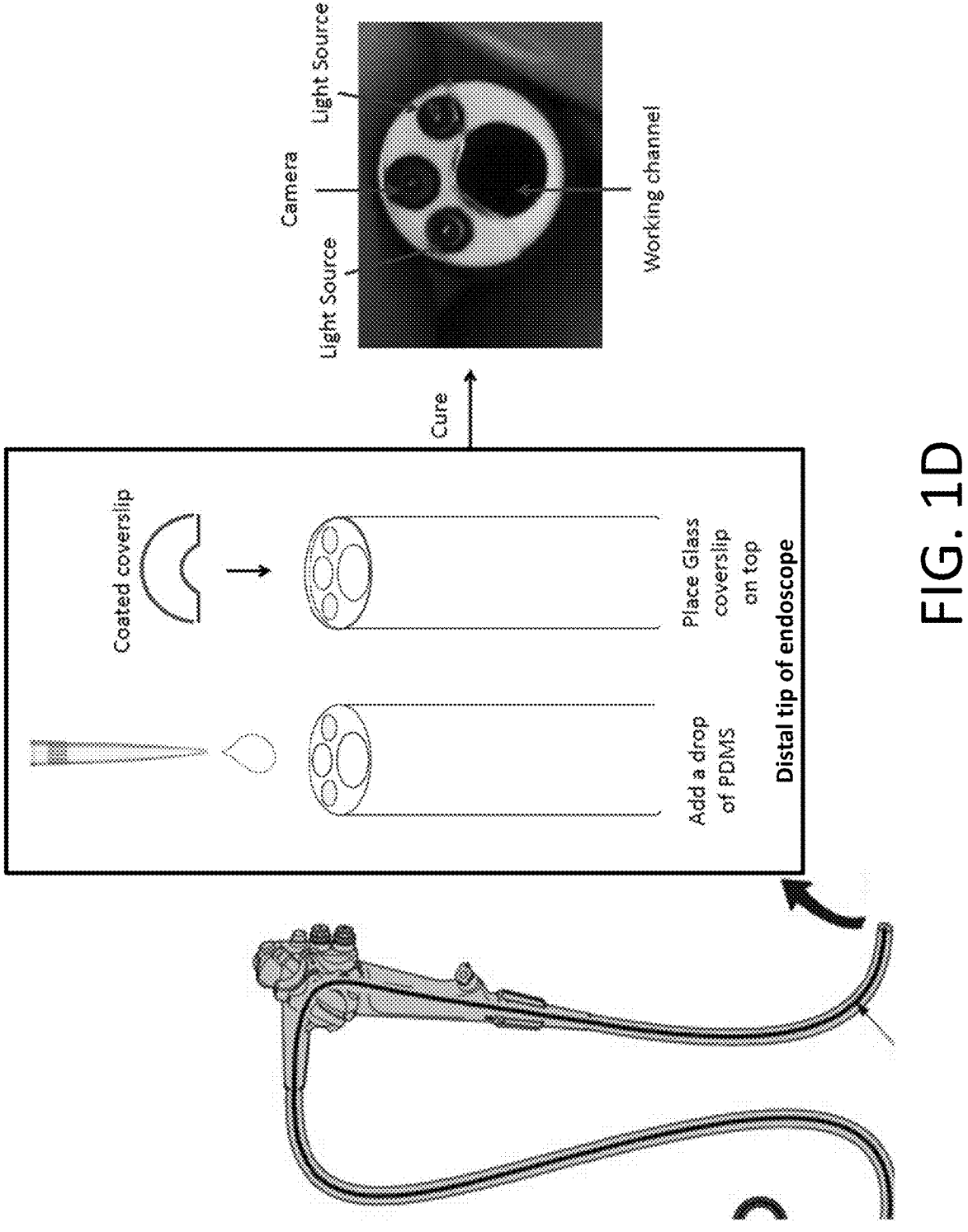

A schematic of one exemplary variant of the overall design of an endoscope window that is coated in a transparent, repellant, liquid-infused coating and a disposable (or permanent) endoscope window that is coated in a transparent, repellant, liquid-infused coating for attachment to the distal end of an endoscope is illustrated in FIGS. 1A-1D. A pipe inspection camera comprising a lens window at the distal end that is modified with a transparent, repellent, oil-infused coating is shown in FIG. 1B. For comparison, the unmodified pipe inspection camera is shown in FIG. 1A. In FIGS. 1C-1D, the distal end of the insertion tube of an endoscope is modified by attaching or affixing a disposable coated glass coverslip. A 6 mm glass coverslip is cut by a diamond scribe in the shape of a crescent to fit over the distal end of the endoscope to cover the lens while leaving the working channel exposed (FIG. 1C(i)). This coverslip is coated with a layer-by-layer based nanoscale surface coating and infused with a lubricating fluid to facilitate repellency (FIG. 1C(ii)). The resulting coating is optically transparent and light transmissive. A drop of polydimethylsiloxane (PDMS) is added to the surface of the distal end of the insertion tube of the scope (FIG. 1C(iii)) prior to fixing the coated glass onto the endoscope lens (FIG. 1C(iv)). The PDMS is cured, thereby securing the coverslip to the surface of the lens (FIG. 1C(v)) while exposing the working channel. This strategy (1) maintains transparency, (2) seals the endoscope lens from contaminating liquids, (3) allows the use of the working channel for various procedures (e.g. suction, irrigation), and (4) enables removal of the coating after the experiments, making multiple repeats possible.

Figures 2A, 2B:
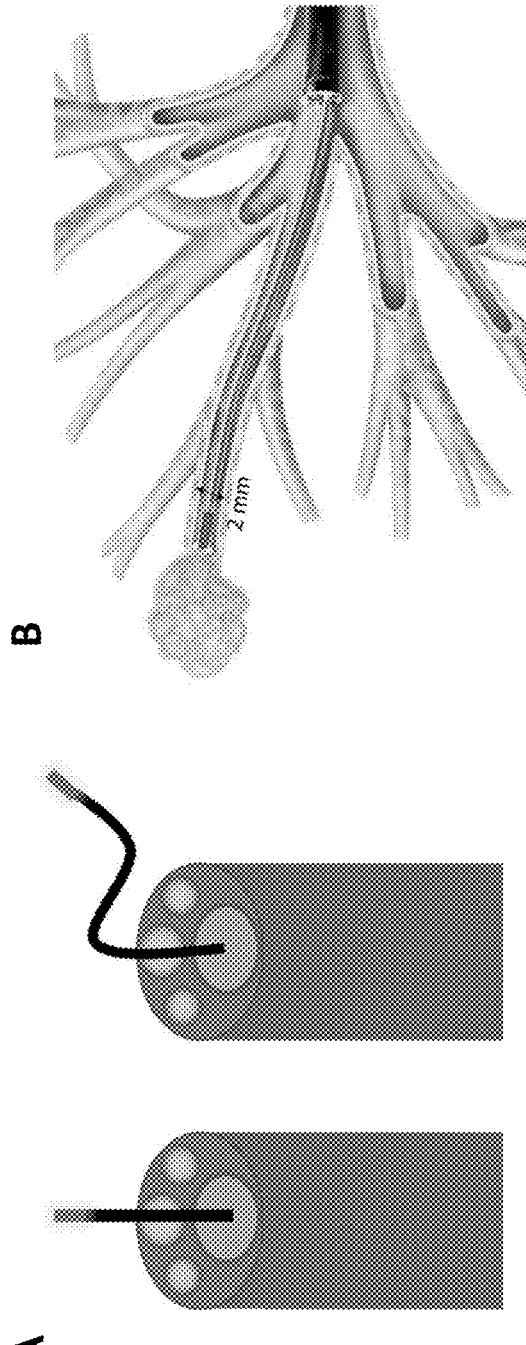
FIG. 2A shows a miniature camera coated with a liquid infused antifouling coating threaded through the existing working channel of an endoscope.
FIG. 2B shows the miniature camera of FIG. 2A threaded through narrow airways in the lungs to image these airways.

In another aspect, an endoscope comprises a miniature camera coated in a transparent, repellent, oil-infused coating, wherein the miniature camera extends from a working channel. As shown in FIG. 2A, a guidewire comprising a miniature camera that is coated with a repellent, oil-infused coating is threaded through an existing working channel of an endoscope. As shown in FIG. 2B, the guidewire and miniature camera are less than 2 mm in diameter and are threaded through an existing working channel into a narrow-diameter hole or opening with a diameter of 2 mm or more. For example, the miniature camera can fit into narrow pathways such as bronchioles (FIG. 2B), allowing for inspection. The miniature camera comprises a CMOS or CCD chip at the distal end that electronically transmits images and is coupled with a light source that is transmitted via a fiber optic bundle. The miniature camera comprises or is modified to comprise a porous surface layer that is optically transparent and light transmissive. In some embodiments, the surface structure of the roughened or porous surface layer comprises feature sizes that are under the diffraction limit. In some embodiments, the surface structure of the roughened or porous surface layer comprises feature sizes that are under the Infiltration of the surface layer with a low surface energy liquid creates an ultra-smooth surface that is slippery and resists or reduces adhesion by particles and immiscible liquids.

In addition to the miniature camera, accessory instruments can be guided into the same working channel. For example, instruments including, but not limited to biopsy needles, forceps, and cytology brushes, can be used in conjunction with the miniature camera in the working channel. The working channel can thus be used to guide both the miniature camera for imaging and an accessory instrument for performing various procedures. For example, narrow pathways such as bronchioles can be imaged and biopsied through the same working channel, providing specimens for histologic or bacteriologic study. The miniature camera can also be used in conjunction with cytology brushes to image and collect cell samples.

An example of a miniature camera that is suitable for use in the present invention is the micro ScoutCam™. The micro ScoutCam™ 1.2 is equipped with a five-lens objective and comprises a disposable CMOS camera which has an outer diameter of only 1.2 mm wide×5 mm long. In some embodiments, the miniature camera has an outer diameter of about 1.2 mm wide. In some embodiments, the miniature camera has an outer diameter of about 1.4 mm wide. In some embodiments, the miniature camera has an outer diameter of about 1.6 mm wide. In some embodiments, the miniature camera has an outer diameter of about 1.8 mm wide. In some embodiments, the miniature camera has an outer diameter of about 2.0 mm wide. In some embodiments, the miniature camera has an outer diameter of about 2.2 mm wide. In some embodiments, the miniature camera has an outer diameter of about 2.4 mm wide. In some embodiments, the miniature camera has an outer diameter of about 2.6 mm wide. In some embodiments, the miniature camera has an outer diameter of about 2.8 mm wide. In some embodiments, the miniature camera has an outer diameter of about 3.0 mm wide. In some embodiments, the miniature camera has an outer diameter of about 6.0 mm wide. In some embodiments, the outer diameter of the endoscope is 12.8 mm. However, the size of the camera is not particularly limited. Other size miniature cameras that are compatible with the particular endoscope model and its intended use are also contemplated for use herein.

In some embodiments, the miniature camera comprises a CMOS camera. In some embodiments, the miniature camera comprises a CCD camera. In some embodiments, the miniature camera is disposable. In some embodiments, the miniature camera is reusable.

In some embodiments, the miniature camera comprises or is modified to comprise a porous surface layer that is optically transparent and light transmissive. In some embodiments, the miniature camera lens comprises or is modified to comprise a porous surface layer that is optically transparent and light transmissive.

Endoscopes that are suitable for use in the present invention include, but are not limited to, arthroscopes, broncho-scopes, colonoscopes, colposcopes, cystoscopes, esophago-scopes, gastroscopes, laparoscopes, laryngoscopes, neuroendoscopes, proctoscopes, sigmoidoscopes, thoraco-scopes, and capsule endoscopy cameras.

In some embodiments, the endoscope comprises a distal window at the distal end of the insertion tube. In some embodiments, the insertion tube of the endoscope is flexible. In some embodiments, the insertion tube of the endoscope is rigid.

Substrate for Lubrication

In one or more aspects, the substrate for lubrication comprises a curved surface and is optically transparent and light transmissive. In other aspects, the substrate for lubrication is optically transparent and light transmissive. In one embodiment, the substrate is a low-surface energy porous solid. It can have a roughened or smooth surface. As used herein, the term "roughened surface" is a substrate that includes both the surface of a three dimensionally porous material as well as solid surface having certain topographies, whether they have regular, quasi-regular, or random patterns. In other embodiments, the substrate is roughened by incorporation of nanotextures. Physically, the large surface area provided by micro/nanoscale roughness not only facilitates complete wetting by the lubricating fluid but also strengthens the adhesion of lubricating fluid within the porous solid.

The geometry of the substrate can be any shape, form, or configuration to suit various-shaped materials and devices. In certain embodiments, the shape is planar. In certain embodiments, the shape is of a crescent.

The roughened surface can be formed in various ways. In some embodiments, the roughened surface is formed by forming pores over a two-dimensionally flat surface to yield a porous material. In some embodiments, the roughened surface is formed by forming pores over a curved surface to yield a porous material. The pores can take any geometry and can have pathways, columns, or more random pathways. The pores can be random or ordered.

A range of surface structures with different feature sizes and porosities can be used. In some embodiments, for optical transparency, feature sizes are under the diffraction limit. In some embodiments, for optical transparency, feature sizes are under 1 nm. In some embodiments, the feature sizes are in the range of about 1 nm to about 200 nanometers. In some embodiments, the feature sizes are in the range of about 1 nm to about 150 nanometers. In some embodiments, the feature sizes are in the range of about 1 nm to about 100 nanometers. In some embodiments, the feature sizes are in the range of about 1 nm to about 85 nanometers. In some embodiments, the feature sizes are in the range of about 1 nm to about 75 nanometers. In some embodiments, the feature sizes are in the range of about 1 nm to about 65 nanometers. In some embodiments, the feature sizes are in the range of about 1 nm to about 50 nanometers. In some embodiments, the feature sizes are in the range of about 1 nm to about 35 nanometers. In some embodiments, the feature sizes are in the range of about 1 nm to about 25 nanometers. The feature sizes can have aspect ratios (height to a characteristic perpendicular dimension) from about 1:1 to 20:1, more particularly from about 1:1 to 10:1.

In certain embodiments, the surface has a large surface area that is readily wetted by the lubricating fluid and which entrains lubricating fluid and retains it on the substrate surface.

The roughened surface material can be selected to be chemically inert to the lubricating fluid and to have good wetting properties with respect to lubricating fluid. In addition, the roughened surface topographies can be varied over a range of geometries and size scale to provide the desired interaction, e.g., wettability, with lubricating fluid. Non-limiting examples of porous or rough surface structures that are optically transparent and light transmissive that can be used include polymers (e.g., PDMS) and hydrophobic porous materials. For example, the roughened surface can be manufactured from, but not limited to, glass, optical glass, sapphire, acrylic, polycarbonate, polyacrylic, polysulfone, polyethylene, polypropylene, and polyurethane. In certain embodiments, the roughened surface comprises PDMS. In certain embodiments, the roughened surface comprises glass. In certain embodiments, the roughened surface comprises optical glass. In certain embodiments, the roughened surface comprises sapphire. In certain embodiments, the roughened surface comprises acrylic. In certain embodiments, the roughened surface comprises polycarbonate. In certain embodiments, the roughened surface comprises polyacrylic. In certain embodiments, the roughened surface comprises polysulfone. In certain embodiments, the roughened surface comprises polyethylene. In certain embodiments, the roughened surface comprises polypropylene. In certain embodiments, the roughened surface comprises polyurethane.

In certain embodiments, the roughened surface may be the surface of a three-dimensionally porous material. The porous material can be any suitable porous network having a sufficient thickness to stabilize lubricating fluid, such as a thickness from about 500 nm to about 10 μm, or from about 5 μm to about 1 mm. In some embodiments, the thickness is from about 500 nm to about 10 μm. Moreover, the porous material can have any suitable pore sizes to stabilize the lubricating fluid, such as from about sub-1 nm to about 200 μm. In some embodiments, the pore sizes are are in the range of about 1 nm to about 200 nanometers. In some embodiments, the pore sizes are in the range of about 1 nm to about 150 nanometers. In some embodiments, the pore sizes are in the range of about 1 nm to about 100 nanometers. In some embodiments, the pore sizes are in the range of about 1 nm to about 85 nanometers. In some embodiments, the pore sizes are in the range of about 1 nm to about 75 nanometers. In some embodiments, the pore sizes are in the range of about 1 nm to about 65 nanometers. In some embodiments, the pore sizes are in the range of about 1 nm to about 50 nanometers. In some embodiments, the pore sizes are in the range of about 1 nm to about 35 nanometers. In some embodiments, the pore sizes are in the range of about 1 nm to about 25 nanometers.

In other embodiments, a roughened surface that is optically transparent and light transmissive is further functionalized to improve wetting by lubricating fluid. Surface coating can be achieved by methods well known in the art, including plasma assisted chemical vapor deposition, chemical functionalization, solution deposition, and vapor deposition. For example, surfaces containing hydroxyl groups (i.e., —OH) can be functionalized with various commercially available fluorosilanes (e.g., (1H,1H,2H,2H-tridecafluorooctyl)-trichlorosilane) or hydrocarbon based silanes (e.g., dodecyl-trichlorosilane) to improve wetting by low surface tension fluids but also maintain transparency. Functionalization of the surface is not limited to fluorosilane functionalization or hydrocarbon functionalization. The surface can be functionalized to create a charged surface, for example, by treatment with 1-Butyl-3-methylimidazolium bis(trifluoromethylsulfonyl)imide. The surface can also be functionalized to introduce amine groups or carboxylic acid groups to the surface. Functionalization can be selected based on the lubricating fluid to be used. Matching the surface chemistry of the lubricating fluid with the functionalized surface structures creates a strong affinity and leads to a minimization of the total surface energy for a solid/lubricant/liquid system in which a second, immiscible liquid is not in contact with the solid substrate. In certain embodiments, many materials having native oxides, such as glass, can be activated to contain —OH functional groups using techniques such as plasma treatment. After activation, either vapor or solution deposition techniques can be used to attach, through an appropriate chemical reaction, silanes, so that surfaces with low surface energy can be produced. For vapor deposition, the deposition can be carried out by exposing the surface to vapors of reactive silanes. For solution deposition, the deposition can be carried out by immersing the surface in a solution of a reactive silane, followed by rinsing and blow-drying after deposition.

In certain embodiments, a layer-by-layer process to alternately assemble positively charged polyelectrolytes and negatively charged silica nanoparticles onto a given substrate is utilized. The surface coating can be achieved by first introducing negative charges to a substrate. Subsequent layers of positively charged polyelectrolyte and negative charged silica nanoparticles are then adsorbed to form a hybrid thin film that can but does not necessarily have to be calcined to produce a porous silica coating. The small size of the silica nanoparticles applied in the process does not interfere with light of visible wavelengths and, thus, gives rise to a completely transparent coating. Surface modification of the particles by silane chemistry (e.g., fluorosilanization) and infusion of a lubricant with matching chemical composition (e.g., a fluorinated lubricant) creates a stable substrate/lubricant interface that repels any immiscible second liquid.

In certain embodiments, negative charges are created on the substrate by plasma treatment, UV-ozone or immersion in base piranha. In certain embodiments, the substrate is subsequently immersed into a solution of positively charged polyelectrolyte (e.g., poly-diallyldimethyl ammonium chloride, PDADMAC), rinsed and immersed into a solution of negatively charged e.g., LUDOX™ silica nanoparticles. In certain embodiments, the assembled hybrid film is calcined or plasma treated to remove the polymer and leave a disordered, porous silica nanoparticle assembly on the substrate, the surface of which is subsequently silanized with e.g., 1H,1H,2H,2H-(tridecafluorooctyl)-trichlorosilane to introduce fluorinated surface functionalities. In certain embodiments, a fluorinated lubricant oil (e.g., DuPont KRYTOX™ 100), matching the surface chemistry of the coating, is infiltrated into the porous structure. The matching surface chemistry between surface structures and lubricant creates a strong affinity and leads to a minimization of the total surface energy for a solid/lubricant/liquid system in which a second, immiscible liquid is not in contact with the solid substrate.

In certain embodiments, the roughened surface comprises a colloidal monolayer. In certain embodiments, the colloidal monolayer is prepared by preassembling colloids at the air/water interface and subsequently transferring them to the substrate. The liquid nature of the interface provides fluidity necessary to achieve high order and uniform coverage and confines the colloids to a two-dimensional layer. The colloidal monolayer can be backfilled by a silica precursor to form an inverse replica that serves as a porous layer to lock-in the lubricant. The regular arrangement of colloids in a monolayer allows for precise calculation and control of surface roughness. The silica backfilling allows for strong, covalent bonding of the nanostructured film to glass or oxide substrates, preventing delamination or adhesive failure of the film and thus enhancing the robustness of the surface structures. SLIPS surfaces exhibiting improved stability are disclosed in International Patent Application No. PCT/US2013/50343, the contents of which are hereby incorporated by reference. Additionally, it can be modified by silane chemistry that provides a broad range of stable, covalently bound monolayers terminated with surface functionalities matched to the properties of the lubricant. The pore size of the inverse monolayers can be adjusted by changing the colloid size while maintaining close-packed order, homogeneity, and regularity. The tunability of pore sizes at the nanometer scale can be used to engineer the optical properties of materials across a wide range of wavelengths and enables the formation of transparent surface coatings.

In certain embodiments, the colloidal monolayer is back-filled with silica precursor solution of tetraethylorthosilicate (TEOS). In certain embodiments, and the organic colloids are combusted to give rise to an inverse structure composed of silica. In certain embodiments, the surface is functionalized to match the chemical nature of the lubricant that is to be added. For example, fluorosilanization of the surface with (1H,1H,2H,2H-tridecafluorooctyl)-trichlorosilane matches the surface chemistry of the inverse colloidal structure to the chemical nature of the perfluorinated lubricant (DuPont KRYTOX™ 100) that consequently wicks into the porous network and forms a stable liquid film held in place by the nanostructures. A person skilled in the art would recognize that other sol-gel precursors to silica or to other metal oxides, as well as their mixtures, can be used in place of TEOS to produce the desired structural features of the substrate while maintaining optical transparency. The list of said metal oxides includes, but is not limited to alumina, Titania, zirconia, hafnia, yttria, rare earth metal oxides and mixtures thereof.

In certain embodiments, the roughened surface has pores that are smaller than the material to be repelled. For example, pore sizes that are smaller than the size of protozoa (e.g., 10 μm), bacteria (e.g., 1 μm), viruses (e.g., 0.1 μm), and the like can be utilized.

In other embodiments, the solid substrate is a polymer infiltrated with lubricating liquid. The slippery surfaces can form by combining lubricating liquids and polymers such that the polymers absorb the liquids and form a lubricating layer on a surface of the polymers (referred to herein also as "self-lubricating polymers"). The self-lubricating polymer includes a cross-linked polymer (e.g., such as a rubber or elastomer) that is solvated with a liquid having a chemical affinity for that polymer material. The chemical affinity creates a solvent effect that causes the polymer to absorb an amount of the liquid and swell. A cross-linked polymer is capable of increasing its volume up to several folds by absorbing large amounts of solvent. The swollen polymer network is held together by molecular strands that are connected by chemical bonds (cross-links). A cross-linked polymer is capable of increasing its volume several folds by absorbing large amounts of solvent. The liquid absorbing effects noted herein are distinguished from capillary action of liquids in nano- and microporous media in that the interaction is on a molecular level. That is, the lubricating liquid interacts with the polymer due to intermolecular interactions such as solvation. To swell the polymer, the enthalpy of mixing between the polymer and the lubricating liquid should be sufficiently low, so that they mix readily with each other when mixed together, and/or undergo energetically favorable chemical interactions between each other. In comparison, capillary effects are driven by the surface energy considerations at the interface of a solid and a liquid, resulting in wicking of the liquid into well-defined pre-existing microscopic channels without swelling of the underlying solid. With proper combinations of the lubricant and polymer (e.g., based on the application, as described herein), the lubricant-polymer materials possess self-replenishing, non-sticking, slippery behavior. The lubricating liquid is selected such that it has an affinity for the polymer, causing the polymer to absorb the liquid and accumulate a lubricant layer of the liquid at the surface of the polymer.

The disclosed self-lubricating polymer can be made from a broad range of polymers and lubricating liquids. The polymer material can be chosen from a wide range of rubbers and elastomers, and other polymers, which can swell significantly in the presence of certain solvent lubricating liquids. In particular, the polymer can be rubber or elastomeric polymers, which are known to swell in the presence of an appropriate solvating liquid. In some embodiments, the polymer is a nonporous material. The polymer, e.g., an elastomer or rubber, is typically a covalently cross-linked polymer. The polymer can be a simple single polymer or complex mixture of polymers, such as polymer blends or co-polymers and the like. The nature and degree of cross-linking can change the properties of the polymer. For example, cross-linking density can be used to control how much the polymer will swell (e.g., a lightly cross-linked polymer may swell more than a highly cross-linked polymer). In other embodiments, the crosslinks can be physical and therefore reversible and/or readily disruptible by solvation so that the swelling ratio is large and/or the swelling rate is high. In some embodiments, the polymer is a copolymer or blend polymer or a composite material (e.g., a mixture of polymers containing nanoparticles or microscale filler materials). In some embodiments, the polymer is a copolymer of covalently and physically cross-linked blocks. In some embodiments, the polymer can be patterned into regions that would subsequently have different degrees of swelling upon lubricant infusion. Further detail on self-lubricating polymers can be found at WO 2014/012080, which is incorporated in its entirety by reference. In other embodiments, the solid substrate is smooth and functionalized to hold the lubricating fluid. In one or more embodiments, the substrate has an anchoring layer. The anchoring layer comprises a head group that is attached to the substrate and a functional group, which is directly or indirectly attached to the head group. The article also has a lubricating layer that comprises a lubricating liquid, which has an affinity for the functional group. The anchoring layer includes moieties having head groups that interact preferentially with the underlying surface and present functional groups to the environment that have surface properties that interact favorably with the lubricating liquid. The lubricating layer is disposed over the anchoring layer, and the layers are held together by non-covalent attractive forces. Further detail on self-lubricating polymers can be found at PCT/US2013/021056, which is incorporated in its entirety by reference.

The Lubricating Fluids

The lubricating fluids used to facilitate repellency and provide transparency are selected to create a fluid surface that is intrinsically smooth, stable, and defect free. The lubricating fluid should infiltrate, wet, and stably adhere to the substrate. Moreover, it should be chemically inert with respect to the solid substrate and the fluid to be repelled. The lubricating fluid should provide transparency and be non-toxic. Further, the lubricating fluid is capable of repelling immiscible fluids of any surface tension. In one or more aspects, the lubricating fluid is a chemically-inert and high-density biocompatible fluid.

Further, the lubricating fluid is capable of repelling immiscible fluids, and in particular biological fluids of any surface tension. For example, the enthalpy or free energy of mixing between the fluid to be repelled and lubricating fluids be may be sufficiently high (e.g., water and oil) that they phase separate from each other when mixed together.

In one or more embodiments, lubricating fluid is inert with respect to the solid surface and biological fluid. Lubricating fluid flows readily into the recesses of the roughened surface and generally possesses the ability to form an ultra-smooth surface when provided over the roughened surface.

Lubricating fluid can be selected from a number of different fluids. These fluids can be selected based on their optical properties, biocompatibility, low (or high) toxicity, anti-clotting performance, and chemical stability under physiological conditions. In one or more aspects, the lubricating fluid is a chemically inert, high-density biocompatible fluid, non-limiting examples of which include perfluoropolyethers (such as KRYTOX™ family of lubricants by DuPont, LUBRILOG LY F, FOMBLIN PPFE Lubricants). In one or more aspects, the lubricating fluid is a perfluoroalkyl, non-limiting examples of which include perfluorotetracosane, hexadecafluoroheptane, and perfluoromethyldecalin. In certain embodiments, the lubricating fluid is KRYTOX™. In certain embodiments, the lubricating fluid is VITREON (by Fluoromed). In certain embodiments, the lubricating fluid is Perfluorodecalin (by Fluoromed). In certain embodiments, the lubricating fluid is a silicone oil. In certain embodiments, the lubricating fluid is a perfluorocarbon oil.

In certain embodiments, the viscosity of the silicone oil is in the range of about 1 to 550 sCt. In certain embodiments, the viscosity of the silicone oil is in the range of about 8 to 550 sCt. In certain embodiments, the viscosity of the silicone oil is in the range of about 10 to 550 sCt. In certain embodiments, the viscosity of the silicone oil is in the range of about 8 to 80 sCt. In certain embodiments, the viscosity of the silicone oil is in the range of about 8 to 350 sCt. In certain embodiments, the viscosity of the silicone oil is in the range of about 80 to 350 sCt. In certain embodiments, the viscosity of the silicone oil is in the range of about 80 to 550 sCt.

The lubricating fluid can also comprise more than one fluid. Lubricating fluid mixtures can comprise, but are not limited to, fluids of different chemical classes of compounds, different viscosities, different surface tensions, and different densities. For example, a lubricating fluid mixture comprising fluids of different viscosities can minimize the reduction in visual clarity due to lubricant trail formation and slow clearance that is observed for higher viscosity silicone oils while maximizing the possible contribution to longevity. In one embodiment, the lubricating fluid comprises 10 cSt silicone oil and 350 cSt silicone oil. In certain embodiments, the lubricating fluid comprises 8 sCt and 350 sCt silicone oil. In certain embodiments, the lubricating fluid comprises 8 sCt and 550 sCt silicone oil. In certain embodiments, the lubricating fluid comprises 10 sCt and 550 sCt silicone oil. In certain embodiments, the lubricating fluid comprises 80 sCt and 550 sCt silicone oil. In certain embodiments, the lubricating fluid comprises 80 sCt and 350 sCt silicone oil.

The ratio of fluids in a lubricating fluid mixture can vary. In one embodiment, the lubricating fluid comprises a 1:1 ratio of two liquids. In certain embodiments, the lubricating fluid comprises a 2:1 ratio of two liquids. In certain embodiments, the lubricating fluid comprises a 3:1 ratio of two liquids. In certain embodiments, the lubricating fluid comprises a 4:1 ratio of two liquids. In certain embodiments, the lubricating fluid comprises a 5:1 ratio of two liquids. In certain embodiments, the lubricating fluid comprises a 10:1 ratio of two liquids. In certain embodiments, the lubricating fluid comprises a 20:1 ratio of two liquids.

In certain embodiments, a lubricating fluid mixture comprising a high viscosity oil and a low viscosity oil will improve longevity while maintaining reasonable mobility of the droplet on the surface. The ratio of the high viscosity oil and low viscosity oil in a lubricating fluid mixture will depend on the endoscopic procedure being performed. For example, in procedures involving heavy bleeding and sticky secretions like mucus, a ratio with higher viscosity lubricant might be preferred to improve the longevity at the cost of slower clearance. In one embodiment, the lubricating fluid comprises a 1:1 ratio of 10 cSt silicone oil and 350 cSt silicone oil.

In certain embodiments, the viscosity of the lubricating fluid, which may comprise more than one fluid, is in the range of about 1 to 550 sCt. In certain embodiments, the viscosity of the lubricating fluid is in the range of about 8 to 550 sCt. In certain embodiments, the viscosity of the lubricating fluid is in the range of about 10 to 550 sCt. In certain embodiments, the viscosity of the lubricating fluid is in the range of about 8 to 70 sCt. In certain embodiments, the viscosity of the lubricating fluid is in the range of about 8 to 80 sCt. In certain embodiments, the viscosity of the lubricating fluid is in the range of about 8 to 350 sCt. In certain embodiments, the viscosity of the lubricating fluid is in the range of about 70 to 350 sCt. In certain embodiments, the viscosity of the lubricating fluid is in the range of about 80 to 350 sCt. In certain embodiments, the viscosity of the lubricating fluid is in the range of about 70 to 550 sCt. In certain embodiments, the viscosity of the lubricating fluid is in the range of about 80 to 550 sCt.

Lubricating fluid can be deposited in any desired thickness, provided the top surface of lubricating fluid forms an ultra-smooth surface and is retained and interacts with the underlying surface. If the liquid layer is too thick, the upper surface is 'unbound' from the underlying surface and will flow with a liquid contacting the SLIPS surface. The liquid layer that interacts with and is retained by the underlying surface is referred to as the 'characteristic thickness' of the liquid layer. The characteristic thickness will vary depending on the underlying surface and the ambient conditions, e.g., temperature, pressure, etc. In some embodiments, the lubricating fluid is deposited via layer-by-layer deposition. In some embodiments, the lubricating fluid is deposited via spray deposition. In some embodiments, the lubricating fluid is re-deposited on the lens or lens window of an endoscope. In some embodiments, the lubricating fluid is deposited on the lens or lens window of an endoscope to modify an existing layer of lubricating fluid. In some embodiments, the lubricating fluid is deposited via layer-by-layer deposition to modify an existing layer of lubricating fluid. In some embodiments, the lubricating fluid is deposited via spray deposition to modify an existing layer of lubricating fluid.

In certain embodiments, the lubricating fluid prevents the formation of a wrapping layer.

Generally, it may be important to have the chemical nature between the porous solid surface and the lubricating liquid be similar. For example, a non-polar lubricating liquid with fluorocarbon functional groups may adhere well with a porous solid surface that is functionalized with fluorocarbon groups (e.g., —CF$_3$, —CF$_2$). In another example, a polar lubricating liquid may adhere well with a porous solid surface that is functionalized with hydroxyl groups (i.e., —OH).

A detailed discussion of the slippery liquid-infused porous surfaces can be found in PCT Application No. PCT/US2012/021929, entitled "Slippery Liquid-infused Porous Surfaces and Biological Applications Thereof" filed Jan. 19, 2012, and in PCT Application No. PCT/2013/050403, entitled "Multifunctional Repellent Materials" filed Jul. 12, 2013, the contents of each of which are hereby incorporated herein by reference in its entirety.

Solving lens fouling with a new omniphobic material has much broader implications in medicine, far beyond the improvement of visibility presented in the studies described herein. One particular consideration is that liquid-infused surfaces significantly reduce bacterial adhesion which is a key advantage in endoscopy. In one embodiment, endoscopes can be designed such that this coating is applied directly to the distal window of an endoscope or on a disposable cover to be attached to the distal end of an endoscope. Direct application on the distal end, the distal window, or to the length of the entire endoscope would require a simple re-lubrication after standard sterilization protocols which would significantly reduce bacterial adhesion and therefore contamination. A person with appropriate expertise in the field should be able to develop SLIPS coatings that will be compatible with conventional sterilization methodologies, including those that use liquid and gaseous sterilization agents.

Another consideration is the reduction in the length of medical procedures, the associated health care costs, and the potential increase in the number of treatments that could be accommodated in the same length of time as the current procedure: To put the results described herein in perspective, for example, the time required for sample collection during biopsy when no fouling occurs is ~20-25 s. Therefore, the cleaning time after a fouling effect in an uncoated broncho-scope is 2-5 times the length of the sample collection duration, whereas in a coated endoscope it contributes only ~$\frac{1}{6}^{th}$ of the time. Looking at the total duration of one endobronchial biopsy from entry into the intubation channel to exit is ~1 min. These values indicate that physicians spend approximately equal time cleaning the lens as the total procedure in an uncoated bronchoscope, whereas in a coated instrument the cleaning adds merely 5-10% to the total procedure time, and in many cases is not needed at all. Moreover, minimizing the use of suction, irrigation, and rubbing will result in a reduction of probability of tissue damage and associated complications, as well as of patient discomfort. Patient comfort can be further improved by the insertion and removal of a lubricated endoscope.

The findings of the study described herein extend to the use of these optimized surfaces in other industries. Surface modifications on lenses to prevent fouling by contaminating liquids will be beneficial for camera-guided instruments in a variety of applications such as oil field and marine exploration, sanitation inspections, robotics, optical sensors, and medicine. In medicine in particular, endoscopes with an antifouling coating to repel biological fluids will improve optical clarity when imaging.

Reusable endoscopes can benefit from the described repellent coating in order to retain a clear visual field particularly when working channels are not available for saline irrigation to clean fouled lenses. Examples of reusable endoscopes include, but are not limited to neuro endoscopes, arthroscopes, sialendoscopes, sinoscopes, root canal endo-scopes, laryngoscopes, cardiovascular surgery endoscopes, thoracic endoscopes, gastroenterology endoscopes, laparo-scopes, endoscopes in gynecology and urology, rectoscopy, and proctoscopy. The use of these coatings in veterinary endoscopes is also a promising avenue.

All these scenarios benefit from the improved visibility, a reduction in cleaning times and therefore a reduction in overall cost of the procedure provided by transparent repel-lent surfaces. Expected benefits associated with aspects of the present invention would also include a clear visual field for the duration of the procedure and shortening the required time for the procedure, thereby reducing side effects and complications of the procedure typically resulting from its prolonged duration. The instruments described herein also reduce the need to withdraw, clean and reinsert a scope. Direct mistakes of the operator associated with not having a clear visual field during critical moments of the procedure may be avoided or minimized. The use of the devices disclosed herein may also reduce the need for extensive suction and irrigation, thereby reducing the intrinsic dangers and/or potential to cause injury associated with these pro-cesses. Camera-guided procedures conducted in accordance with the methods described herein should result in better and faster diagnosis, sampling, and treatment. Another benefit associated with the devices disclosed herein is the potential to conduct the associated procedures in narrow areas that were previously unreachable with conventional devices. Since the devices disclosed herein require few, if any, suction and/or irrigation channels, procedures with the devices disclosed herein can be conducted in relatively narrow areas that would not have been possible if there had to be room for suction and/or irrigation channels.

EXAMPLES

The following examples further describe and demonstrate embodiments within the scope of the present invention. The examples are given solely for the purpose of illustration and are not to be construed as limitations of the present inven-tion, as many variations thereof are possible without depart-ing from the spirit and scope of the invention.

Example 1

Camera-guided instruments, such as endoscopes, have become an essential component of contemporary medicine. The 15-20 million endoscopies performed per year in the United States alone demonstrate the tremendous impact of the technology. However, doctors heavily rely in real time on the visual feedback provided by the endoscope camera and the effective function of these devices is routinely compromised when body fluids and fogging occlude the lens, requiring lengthy cleaning procedures that include irrigation, tissue rubbing and suction. Bronchoscopies are especially affected because they are performed on a particu-larly delicate tissue, in high-humidity environments with continuous exposure to extremely adhesive biological fluids such as mucus and blood. Described herein is a repellent, liquid-infused coating on an endoscope lens or lens window capable of preventing vision loss after repeated submersions in blood and mucus. The materials properties of the coating, which included conformability, mechanical properties, transparency, oil type and biocompatibility, were optimized in comprehensive in vitro and ex vivo studies. Extensive bronchoscopy procedures performed in vivo on porcine lungs showed significantly reduced fouling, resulting in either unnecessary or ~10-15 times shorter and less intensive lens clearing procedures, compared to an untreated endoscope. The new material described herein opens up opportunities in the design of the next-generation endoscopes that will improve visual field, display unprecedented anti-bacterial and anti-fouling properties, reduce the length of the procedure and enable visualization of currently unreachable parts of the body, thus offering enormous potential for disease diagnosis and treatment.

A layer-by-layer deposition protocol utilizing 20 nm silica particles to create mechanically robust porous silica network that showed strong adhesion to glass due to the final calcination step resulting in no delamination during adhesion tape tests was used. (PCT Application No. PCT/2013/050403, the content of which is hereby incorporated herein by reference in its entirety.) When infused with a liquid, these anti-reflective coatings displayed increased transparency compared to the underlying plain glass. This porous silica network infiltrated with varying oils was first characterized for performance in vitro and ex vivo using a 5.5-mm diameter Eggsnow USB Borescope Endoscope Pipe Inspection Camera, similar in size to an Olympus Bronchoscope (EXERA BF-160) used in our subsequent in vivo experiments (FIG. 1A-1B). A protocol was developed to create a disposable endoscope attachment, by fixing a coated glass coverslip onto the distal end of the endoscope lens via a polydimethylsiloxane (PDMS) adhesion layer (FIGS. 1A-1D). For in vivo studies, a 6 mm glass coverslip was cut in the shape of a crescent to fit over the lens while leaving the working channel exposed (FIGS. 1C-1D). This strategy i) maintains transparency, ii) seals the endoscope lens from contaminating liquids, iii) allows the use of the working channel for various procedures (e.g. suction, irrigation), and iv) enables removal of the coating after the experiments, making multiple repeats possible.

Figures 7A, 7B:
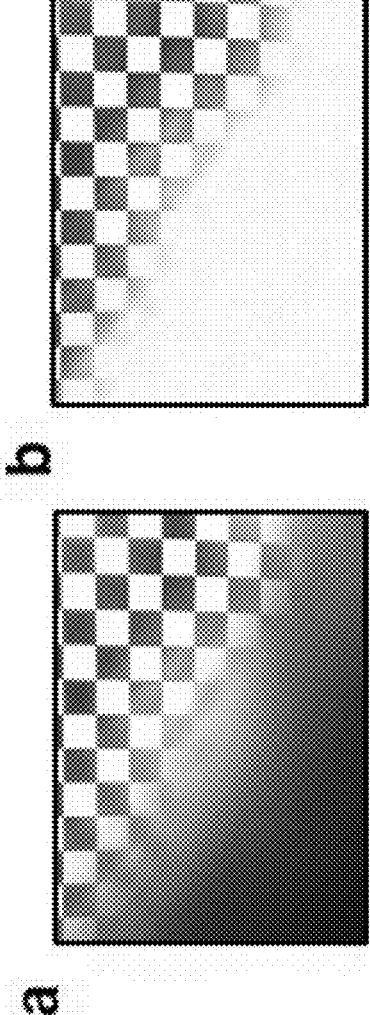
FIGS. 7A-7B show the image analysis for blood and mucus dip experiments. The original image (FIG. 7A) is changed to subtract the background (FIG. 7B).

One of the potential modes of failure for liquid-infused coatings is the depletion of the low-surface-energy lubricant layer from the surface due to the formation of a wrapping layer around the contaminating liquid, leading to liquid pinning on the exposed solid. In the challenging environment, in which endoscopes are used, highly adhesive body fluids will then contaminate the lens or lens window resulting in the reduction of the field of view and the necessity to clear the lens or lens window through extensive irrigation and suction. To estimate the length of the uncompromised lens performance in such conditions, the endoscopes were repeatedly immersed in porcine blood and mucus and characterized the loss of visibility resulting from the lens occlusion. Two classes of commercially available lubricants were tested: silicone oils (Momentive or Gelest polydimethylsiloxanes) and perfluorinated fluids (perfluoroperhydrophenantrene, or VITREON, and perfluoropolyethers, PFPE) (DuPont KRYTOX™ series). These choices were dictated by the physical properties of these liquids (low surface energies, broad ranges of viscosities and volatilities available), their chemical inertness, and prior FDA-approved applications of some of them in clinical settings, such as ophthalmic surgeries. The silicone oils of different viscosities (10, 350, 500 cSt) show stable performance and maintain a remarkably clear field of view after multiple dips of the endoscopes in fresh porcine blood (FIGS. 3A-3D). In contrast, the untreated controls fail immediately after the first contact with blood (see lines connecting circles in FIGS. 3A-3D). The lowest viscosity silicone oil tested (10 cSt) consistently maintain a visual field close to 100% clarity for up to 100 dips in blood for all tested endoscopes (FIGS. 3A-3B) (image analysis is described in FIGS. 7A-7B presents additional view of the resulting repellency properties).

Figure 3A:
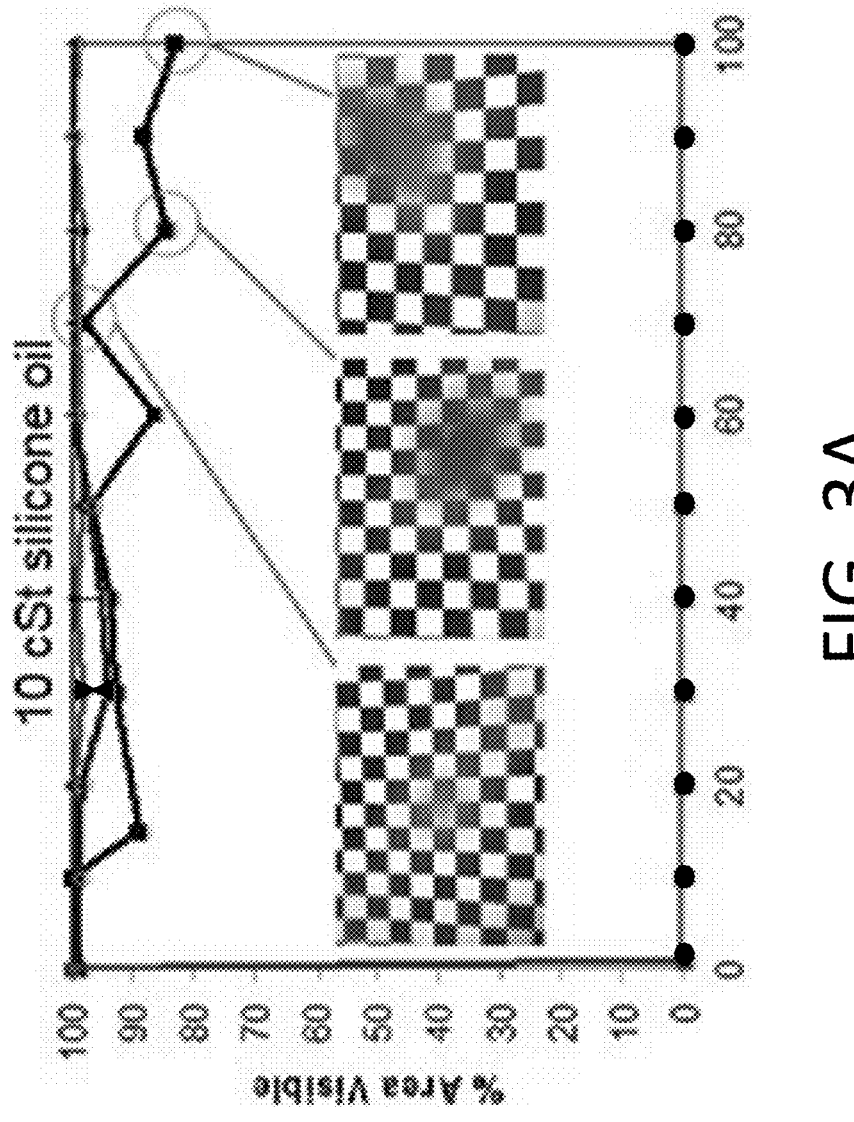
FIGS. 3A-3D shows blood dipping experiments with silicone lubricants of varying viscosity. All experiments were performed in triplicates. Replicates=1 (inverted triangle), 2 (triangle), 3 (square) correspond to each sample tested. The line connecting the circles corresponds to the uncoated endoscope. Dipping was performed in whole porcine blood using endoscopes coated with (FIG. 3A) 10 cSt silicone oil, with insets demonstrating visualization of field of view at 70, 80 and 100 dips for the poorest performing sample.
Figure 3B:
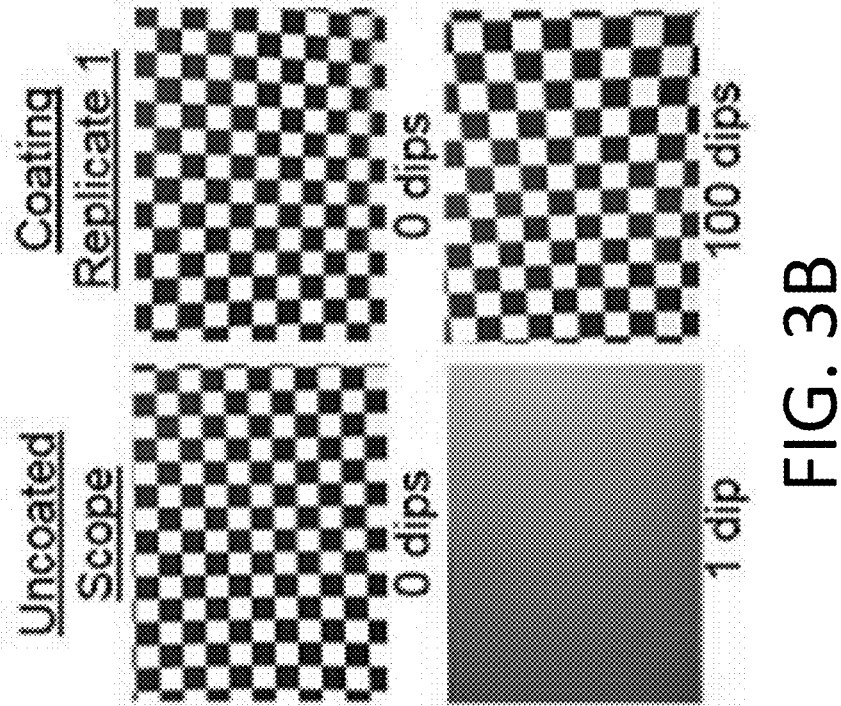
Figure 3C:
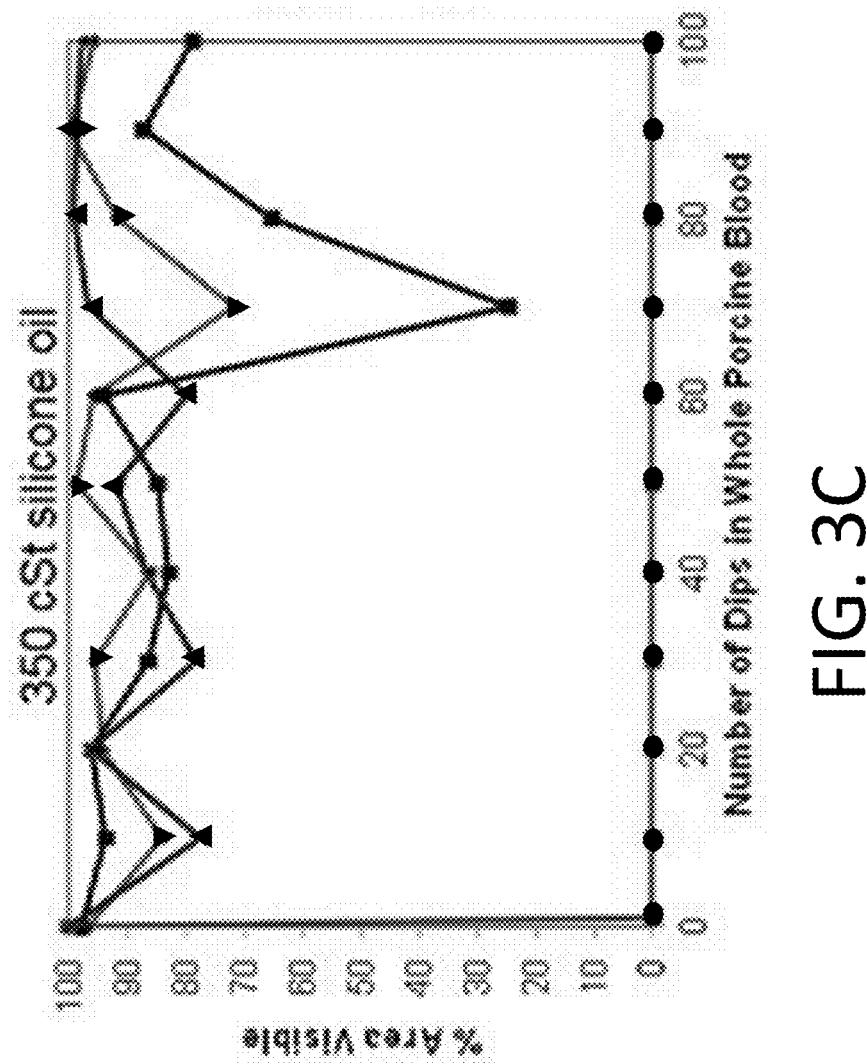
Figure 3D:
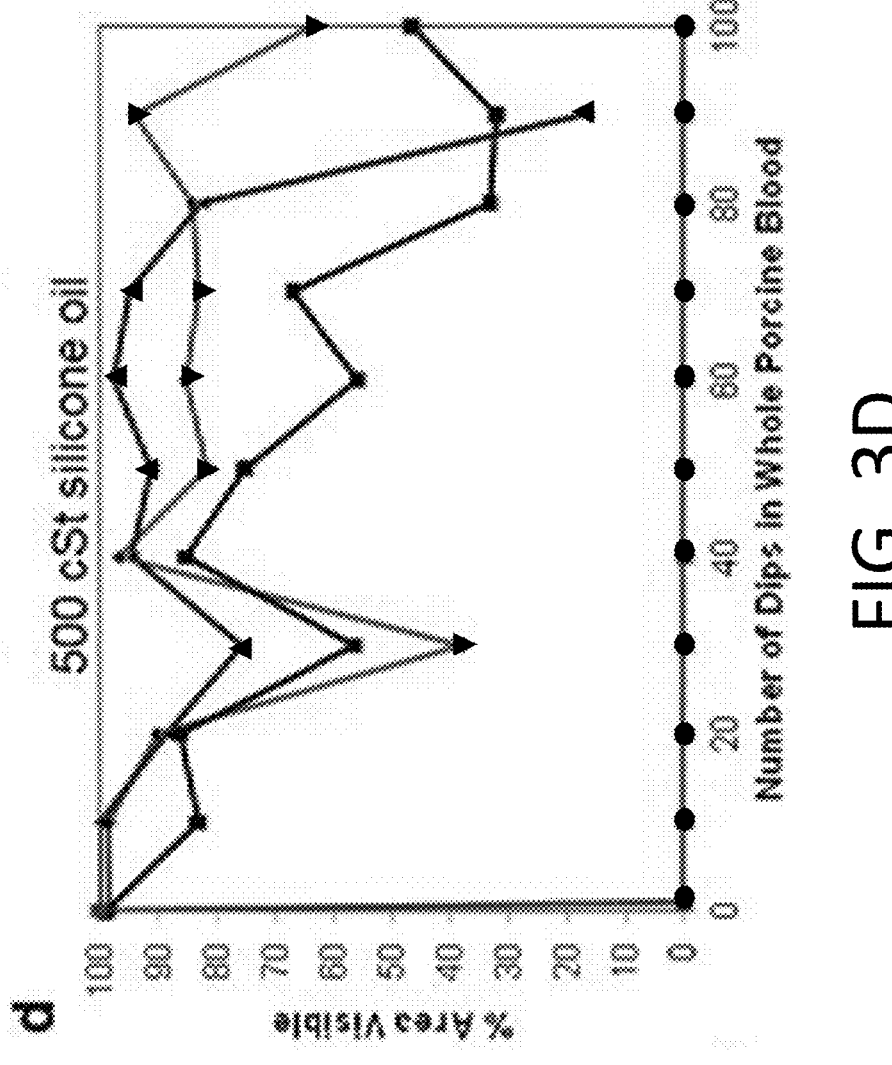
Figure 8:
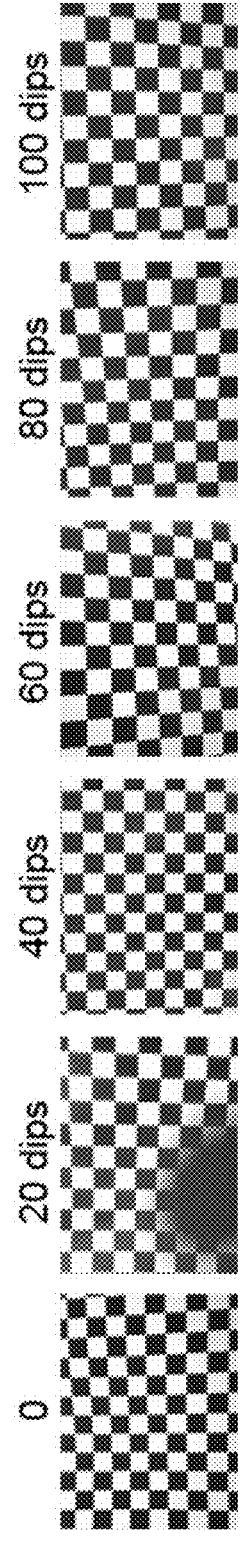
FIG. 8 shows the relubrication of surface coating after 100 dips in porcine blood with 10 cSt silicone oil.

While there is natural variability among the replicates (FIG. 3A, 3C, 3D), several observations can be made: The best sample (line connecting inverted triangle data points) demonstrates 100% clarity for all 100 dips (FIG. 3B), while the poorest performing sample (line connecting square data points) only slightly fouls the lens (reduction in visibility by ~20%). However, this fouling is found to be dynamic in nature: it does not stay pinned, but rather appears in different areas and by repeated dipping is easily removed, bringing the field of view to the original 100% visibility. FIG. 3A clearly demonstrates both the mobility of the blood drop on the lens as well as the oscillatory nature of the experimentally measured field of view. Importantly, it was found that upon contamination, after a gentle water wash and re-lubrication, the coating continues to maintain clarity for at least another 100 dips (FIG. 8). Analogous oscillatory behavior in visualization is also found for the higher viscosity lubricants, but slower equilibration of the oil film deformed upon contact with blood leads to temporary visual aberrations (FIG. 3C, 3D). Perfluorinated lubricants, including FDA-approved VITREON, were also investigated as alternatives to silicone oil. The perfluorinated liquids-based coatings show superior repellency compared to that of the unmodified scopes, but tend to fail faster than their silicone oil-based analogs (after approximately 10, 20, and 30 dips for VITREON, 80 cSt PFPE and 550 cSt PFPE, respectively) (FIGS. 9A-9C; FIGS. 10A-10B), likely caused by the less favorable surface energy relations between the solid substrate and oil.

Figure 4A:
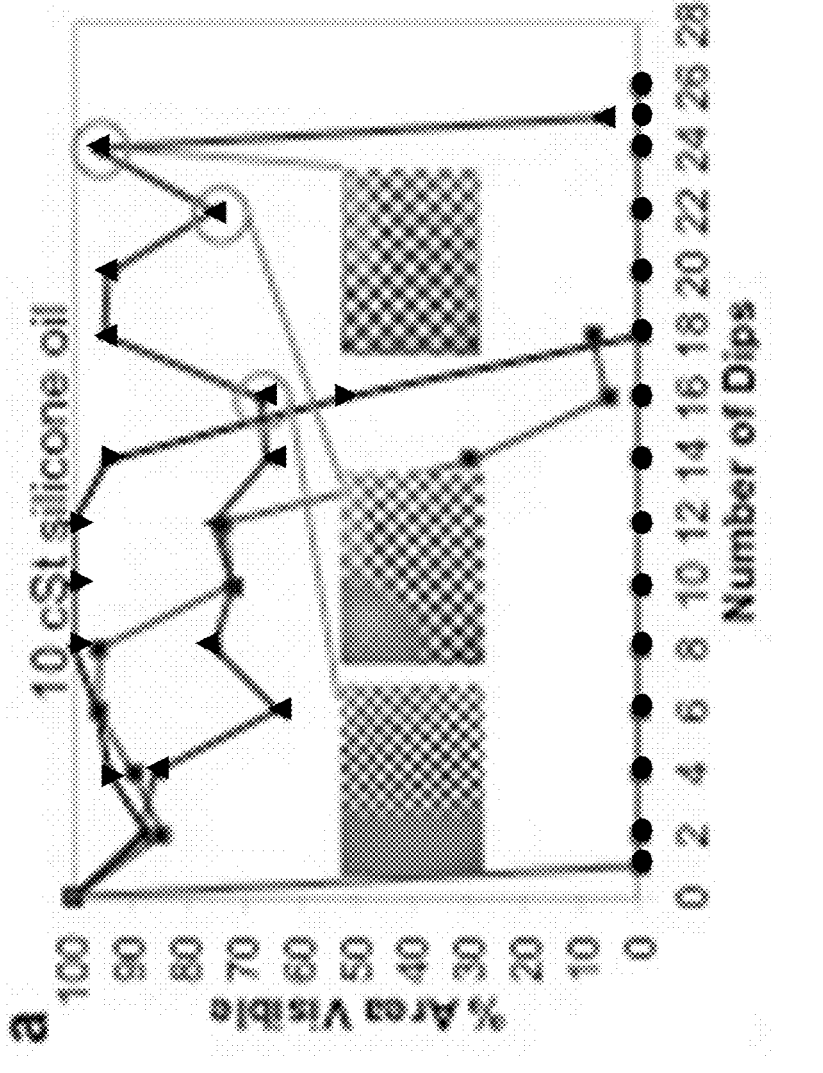
FIGS. 4A-4C show mucus dipping experiments with varying viscosity silicone lubricants. All experiments were performed in triplicates. Replicates=1 (triangle), 2 (square), 3 (inverted triangle) correspond to each sample tested, circles illustrate the performance of an uncoated control. Dipping was performed in 17 wt. % mucin solution using endoscopes coated with (FIG. 4A) 10 cSt silicone oil.
Figure 4B:
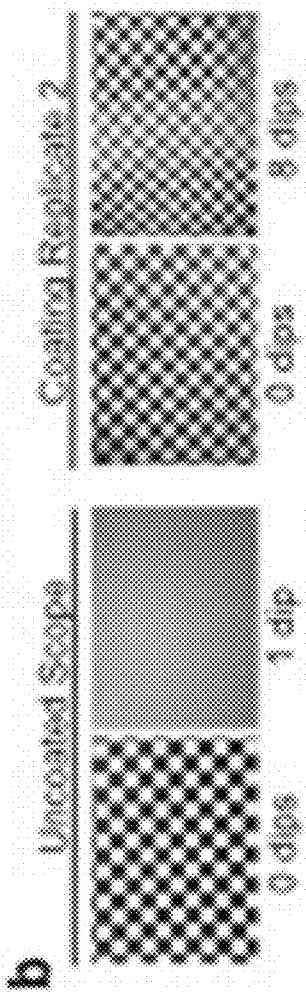
Figure 4C:
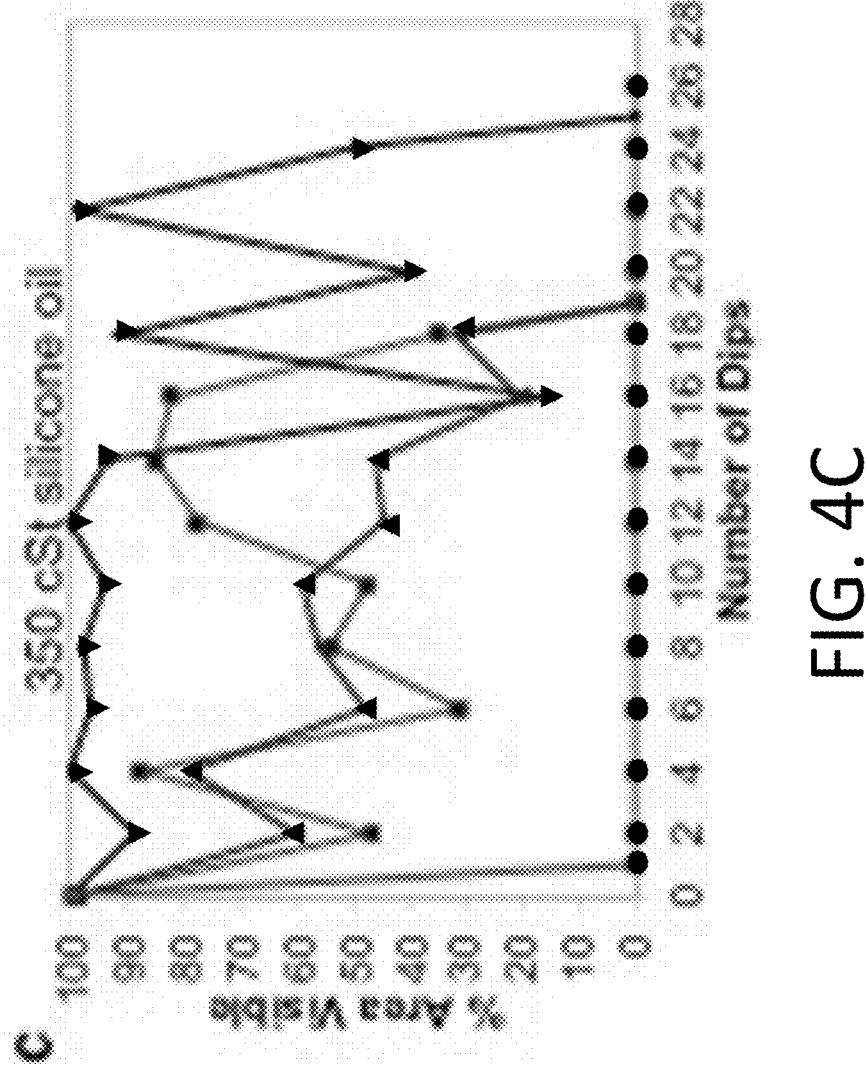

Similarly, the coated endoscopes were immersed into porcine mucin solutions with a concentration (17 wt.-%) typically found in cystic fibrosis patients, a patient population known to have an excess of extremely sticky lung secretions (FIGS. 4A-4C). The mucus was found to be too dynamically inhomogeneous to yield consistent results between different coated samples and repellency seems to be dominated by local variations in viscosity in the mucus solution. Nevertheless, as FIGS. 4A, 4C clearly show, the mucus is more easily shed from the surface lubricated with 10 cSt oil compared to the one lubricated with 350 cSt oil, surviving on average ~20 dips before loss of visual field. As expected, the uncoated control consistently loses visibility after the very first exposure to mucus solution (FIG. 4B). Interestingly, in some cases, even with such a sticky contaminant, both the 10 cSt and 350 cSt oil display an oscillatory behavior in vision reduction demonstrating the capacity for the field of view to be restored after initial fouling by applying continued solution contact (insets in FIG. 4A).

In order to minimize the reduction in visual clarity due to lubricant trail formation and slow clearance that is observed for higher viscosity silicone oils while maximizing their possible contribution to longevity, an endoscope was lubricated with the 10 cSt and 350 cSt oil in a 1:1 ratio. The mixed lubricant has a viscosity of 72 cSt and leads to ~4 times longer coating survival compared to the 10 cSt control (FIGS. 11A-11B), showing that the performance can be further optimized by the application of a mixed-oil coating.

Figure 5A:
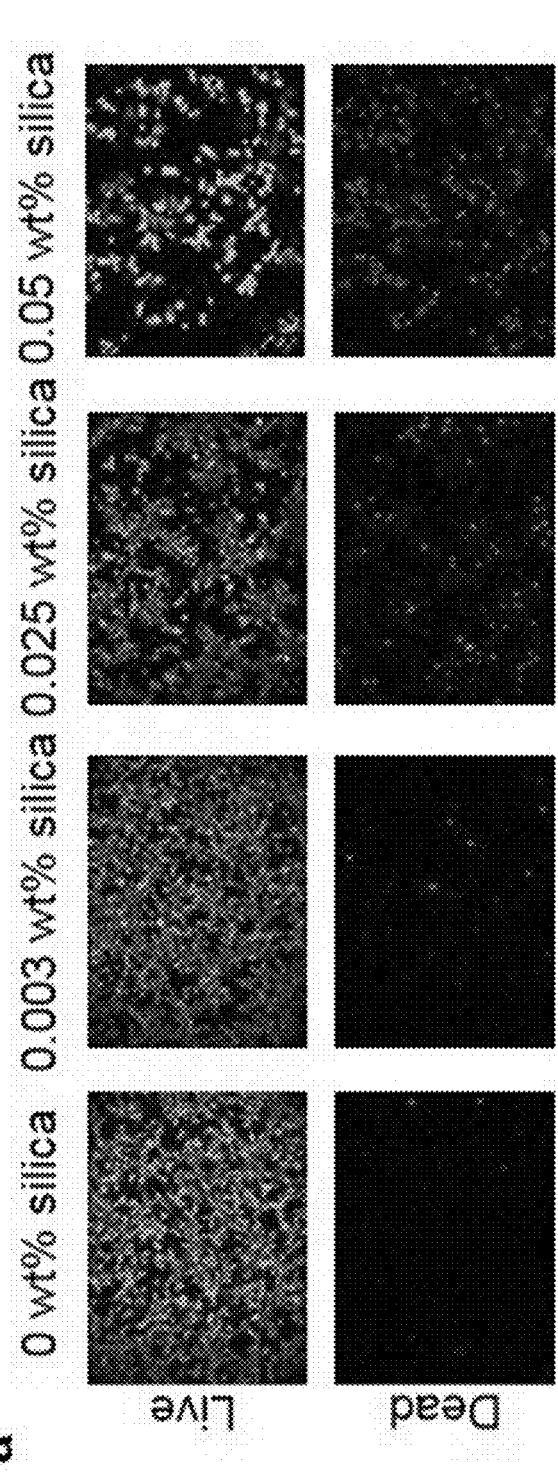
FIGS. 5A-5D show results of experiments aimed at evaluating toxicity of silica nanoparticles and silicone oil.
Figure 13:
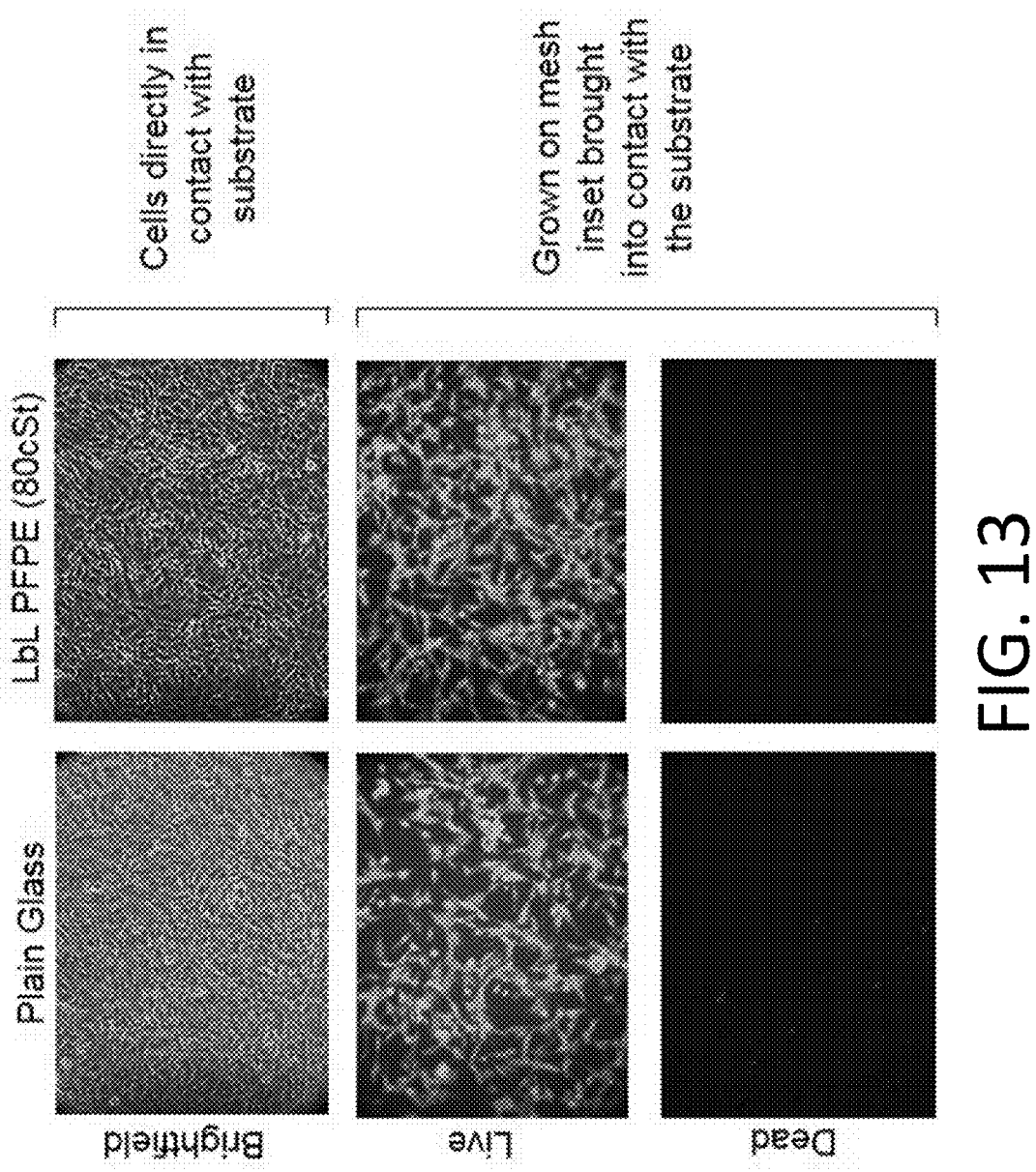
FIG. 13 shows the experimental data aimed at evaluating toxicity of PFPE (80 cST). Toxicity study of PFPE (80 cSt) infused layer-by-layer (LbL) assembled silica particle surfaces. Brightfield images show mesenchymal stem cells that were in contact with plain glass and PFPE infused LbL surfaces for 24 hours of incubation. Calcein AM is used to stain live mesenchymal stem cells grown on a polymer mesh in contact with plain glass and PFPE infused LbL glass in a transwell plate. Cells thrive in the presence of both the plain glass control and the liquid-infused coating. There are negligible dead cells.

To assess potential toxicity of the components of the coating, mouse mesenchymal stem cells in two separate sets of experiments were subjected to the two key components of the coating, i.e., 20 nm silica particles and lubricants (silicone or fluorinated oils). FIG. 5A shows live/dead stains of cells incubated with varying concentrations of silica nanoparticles. Toxicity was quantified by evaluating the area coverage of cells (FIG. 5C, FIG. 13). At the lowest concentration studied, 0.003 wt. %, that is more than four times higher than in the hypothetical worst-case scenario in which the entire coating delaminates from the substrate (corresponding to ~7×10⁻⁴ wt. % of silica particles), minimal dead cells and a live-cell coverage similar to the control were observed, indicating no toxic effects from the silica particles (this concentration falls in the regime indicated by the dotted box in FIG. 5C). Toxicity begins to manifest itself only at a silica particle concentration that is ~35 times higher than that available from the fully delaminated coating. It is noteworthy that the assembled coating provides a very strong bonding of the particles to the substrate, making any removal of nanoparticles from the coating due to mild abrasions with tissue extremely unlikely.

Figure 5B:
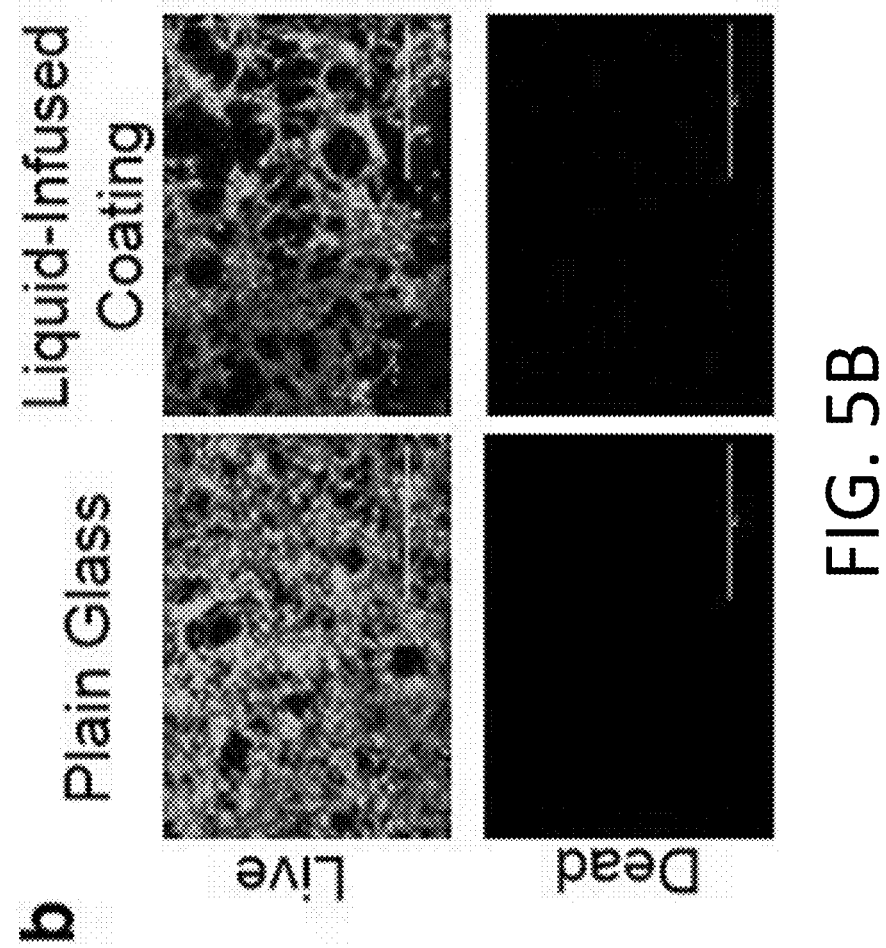
Figure 5C:
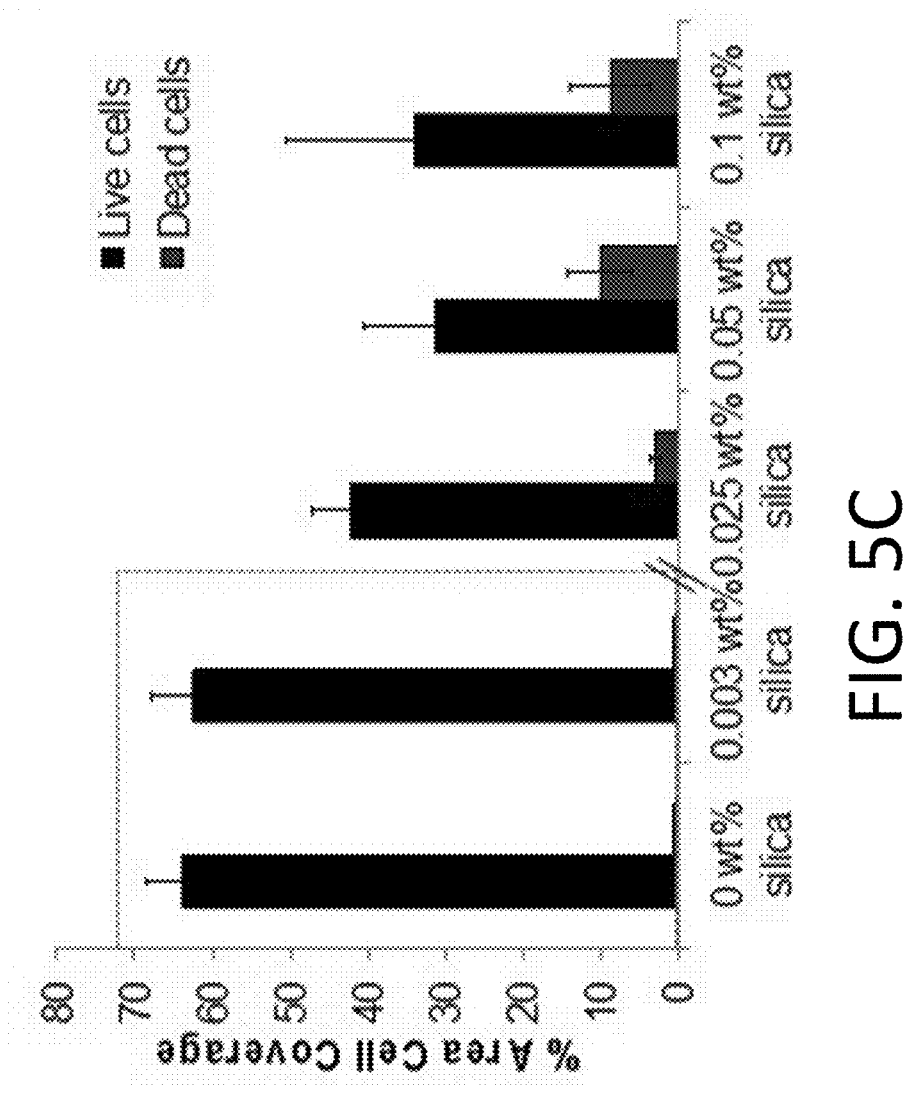
Figure 5D:
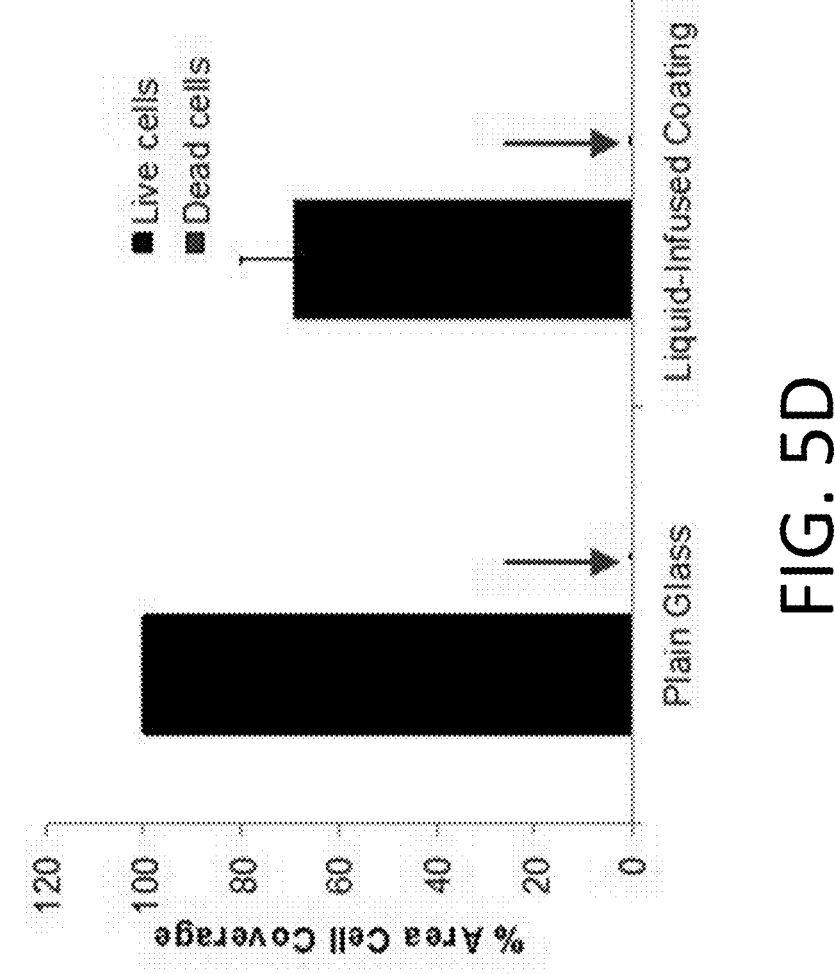

Cells were then grown on a plain glass substrate and on the silicone oil-infused coating for four days to assess toxicity of the lubricant (FIGS. 5B, 5D). Although cells on the lubricant-infused coating show a lower cell coverage (likely caused by the poor adhesion to the repellent coating), the number of dead cells are negligible (FIG. 5D). The effect of the PFPE oil was also evaluated and found to be non-toxic (FIG. 13).

Figure 6A:
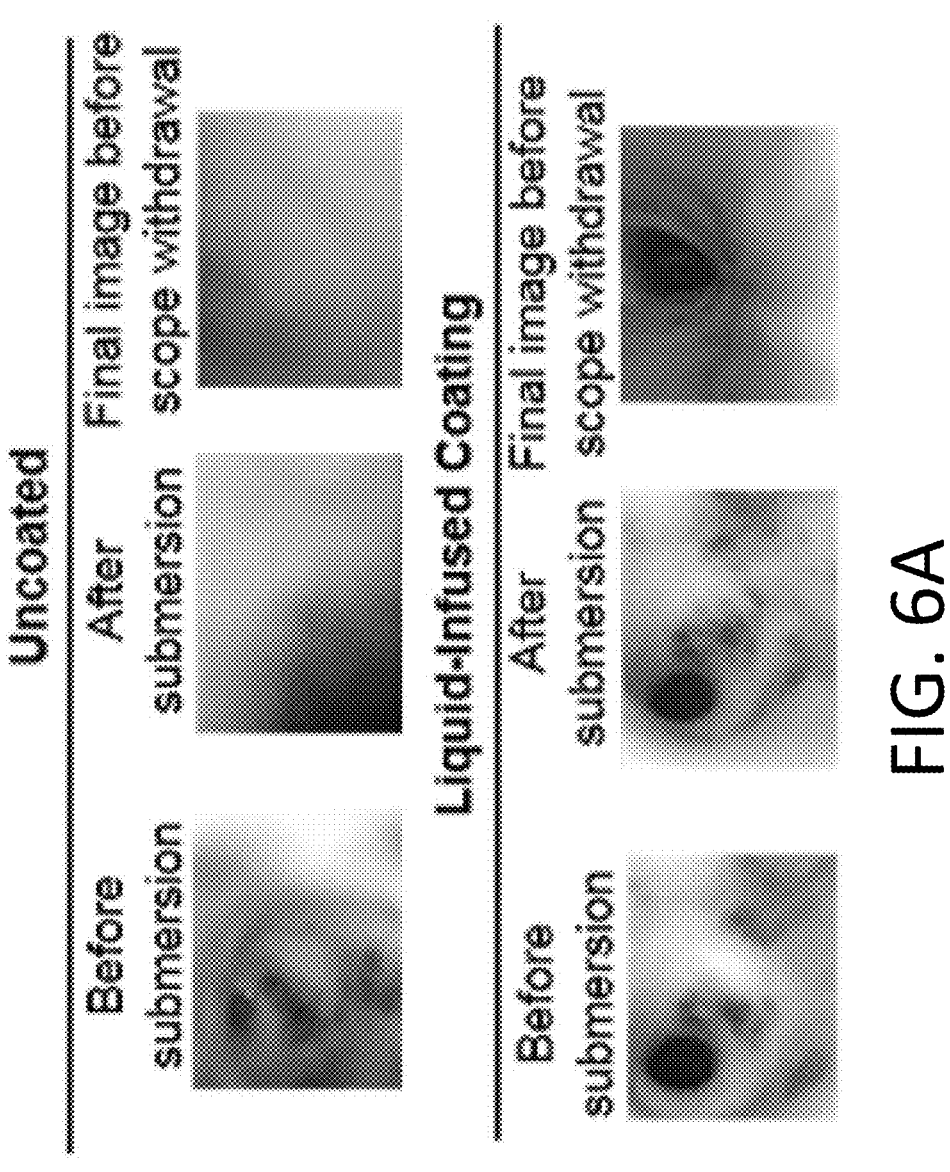
FIGS. 6A-6C show repellency of lung surfactant ex vivo, and in vivo bronchoscopy procedures.

To determine the efficacy of the surface coating to maintain a clear operative field, bronchoscopy was performed in an ex vivo and in vivo porcine lung model. First, an explanted porcine lung was used to test the performance of a coated endoscope against lung surfactant, present to maintain lung compliancy, which due to its interfacial activity may compromise the coating's stability and contribute to impaired vision and fouling. Upon contact with the airway secretions in the explanted lung, the uncoated endoscope is unable to retain a clear field of vision, whereas the perfluorocarbon-based liquid-infused coating easily maintains complete clarity (FIG. 6A). This encouraging result strongly indicates that the antifouling coating may indeed offer significant advantages in clinically important in vivo procedures, which is discussed below.

For this part of the study, the performance of coated bronchoscopes during typical bronchoscopy procedures, such as airway inspections, endobronchial biopsies, and transbronchial biopsies, performed in vivo on porcine lungs was evaluated. In all the procedures, the likelihood of vision loss upon contact with biological material is reduced by more than twice for the coated endoscope, as compared with an uncoated one (the control lost vision in ~50% of all contacts, the coated endoscope in less than 20%). Moreover, these experiments are likely to have overestimated the performance of the uncoated control since residual silicone oil present in the intubation tube and at entry points from the previous experiments using coated endoscopes may have deposited on the control in subsequent experiments, as well, improving its performance.

Figure 6B:
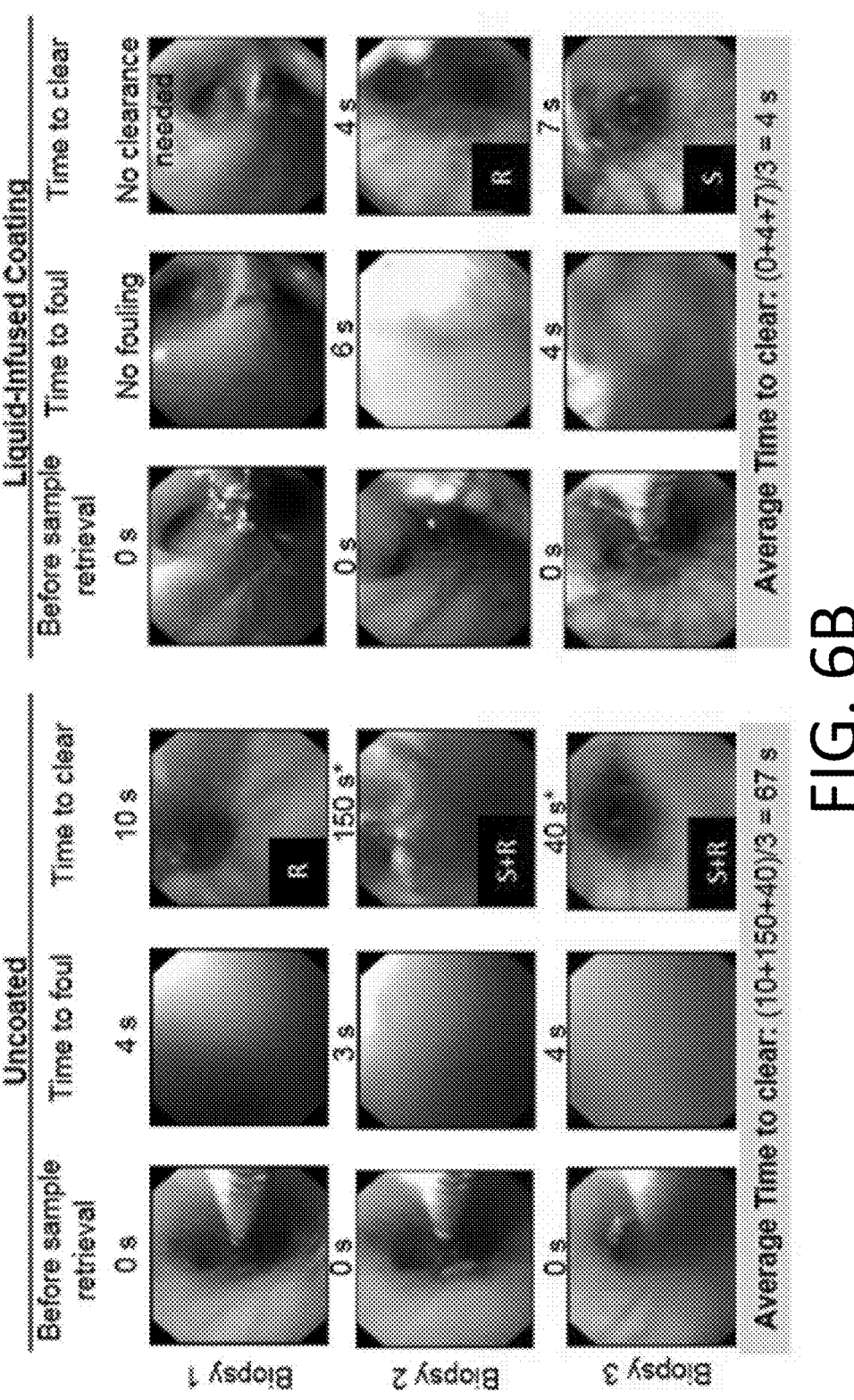

The most striking difference in performance between the liquid-infused coating and the uncoated bronchoscope is observed during endobronchial biopsies where forceps are used to sample the carina. Upon withdrawal of the forceps, contact of the bronchoscope with the bleeding carina induces complete vision loss. FIG. 6B summarizes the performance of the liquid-infused coating compared to the uncoated bronchoscope when both bronchoscopes are exposed to similar levels of bleeding. Of the three times that the biopsy is performed, the uncoated bronchoscope loses visibility all three times (FIG. 6B,). Clearance on average takes more than 1 min. In two instances, visibility is not completely retained even after intermittent rubbing and suction, leading to blind operation for more than 2 min. In contrast, the bronchoscope coated with the liquid-infused coating maintains a clear field of vision (biopsy 1) or, if vision loss occurs, restoration of visibility occurs rapidly (on average, in just 4 s) and with minor efforts (short contact to the wall or short suction to remove pooled blood) (FIG. 6B.

Figure 6C:
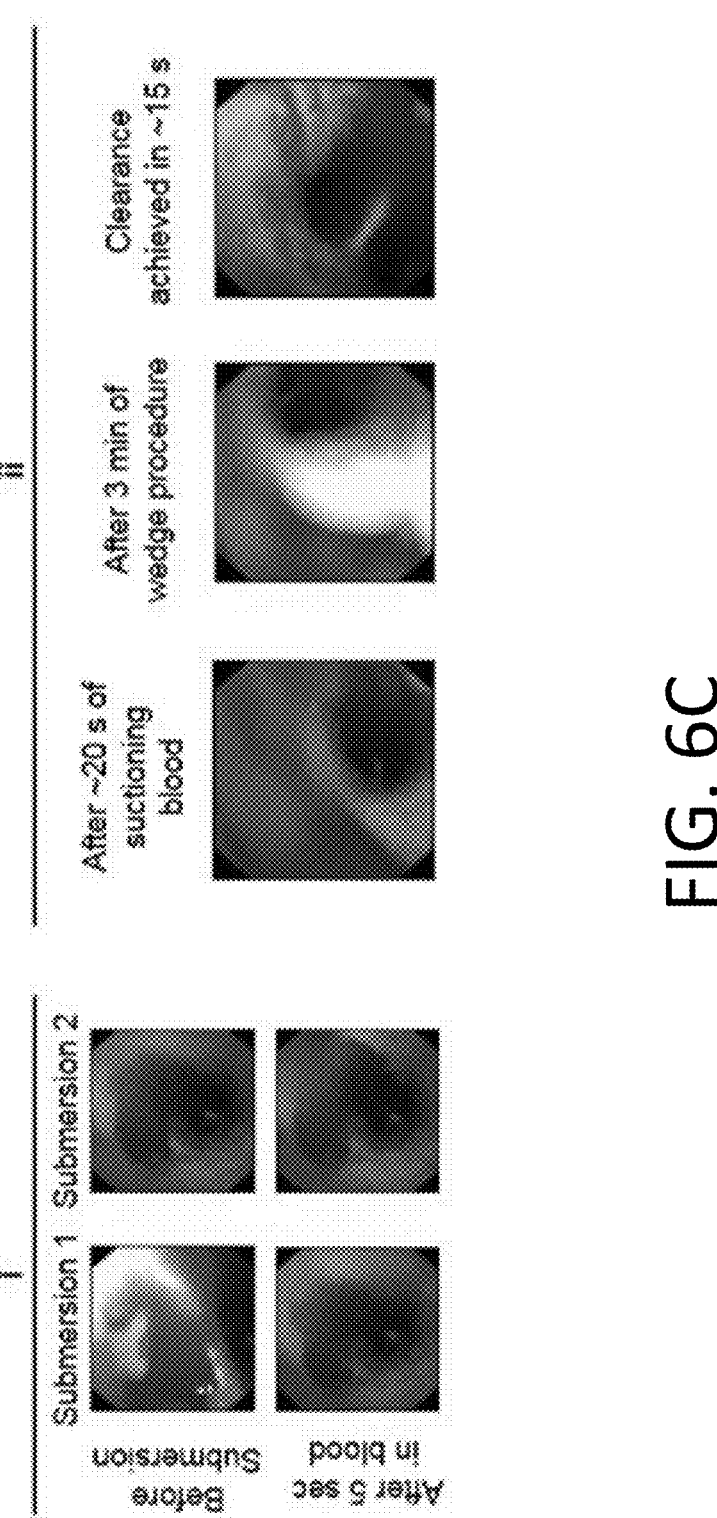

After a transbronchial biopsy with the coated bronchoscope, significant bleeding necessitated the performance of a wedge, the procedure, in which the bronchoscope is used to press against the bleeding site and form a plug that stops the blood flow and facilitates clotting to induce hemostasis. After two 5 s submersions in blood, the field of vision is completely clear (FIG. 6C(i)). Approximately 20 s of extensive suction, which is applied to remove the blood from the surrounding area before the wedge, results in ~50% fouling of the lens area and partial loss in vision (FIG. 6C(ii)). However, clarity is sufficient to allow the operator to visualize the airway, guide the bronchoscope to the site of bleeding and perform the wedge in this critical situation involving bronchoscope exposure to a substantial amount of blood and to shear conditions imposed by the suction procedure. After three minutes, the bronchoscope is withdrawn from the bleeding site and remarkably, more than 50% of the visual field remains clear, with occlusion occurring exclusively at the edge of the lens (quite likely due to edge effects whereby the blood adherence starts on the uncoated sides of the endoscope). Short contact with the airway wall and suction completely clears the lens within seconds (FIG. 6C(ii)). This exceptional performance of the coated scope during extensive bleeding demonstrates the potential of the coating in one of the harshest environments encountered in bronchoscopy.

The studies described herein demonstrate that a lubricant-infused coating applied on endoscope lens or lens windows provides unprecedented clarity of visual field upon contacts with a range of highly contaminating bodily fluids. A coating infused with 10 cSt silicone oil is shown to consistently repel blood when repeatedly submerged in it, up to 100 immersions, and not losing more than 20% visibility, while the uncoated scope loses 100% of the field of view immediately upon submersion. The former also drastically improves the repellency of mucus and lung surfactant. In vitro toxicity tests do not indicate any adverse effects of the coatings. Based on the highly promising in vitro and ex vivo repellency results and the associated visualization capabilities, the best performing coatings were used in multiple bronchoscopies performed in vivo on porcine lungs. A range of clinically relevant procedures (endobronchial biopsy, transbronchial biopsy, and transbronchial brushing) demonstrate that these antifouling liquid-infused coatings prevent blood occlusion, and drastically reduce the clearance time needed to completely regain visibility, even in harsh environments involving strong bleeding. In contrast, the visual field of the uncoated endoscopes in both ex vivo and in vivo procedures are immediately compromised under the same experimental conditions and require extended (10-15 times longer) clearance times.

Methods

Materials

Poly(diallyldimethylammonium) chloride (20% in water), Ludox TM40 silica nanoparticles (diameter: 20 nm), (1H, 1H,2H,2H-tridecafluorooctyl)-trichlorosilane, decyltrichlorosilane, and mucin from porcine stomach lining type II were purchased from Sigma Aldrich and used without further purification. MilliQ (Millipore, Billerica, MA, USA) water was used for all experiments. The DuPont KRY-TOX™ PFPE GPL 103 (80 cSt), and 105 (550 cSt) lubricants were purchased from Miller-Stephenson. VITREON (perfluoroperhydrophenanthrene) was purchased from Fluoromed LP. Silicone oil was purchased from Momentive (10 cSt silicone oil) and Gelest (350 cSt and 500 cSt). Glass coverslips (22×30 mm, No. 1.5) were purchased from VWR. Whole porcine blood (Na Heparinized 100 mL) was purchased from Lampire Biological Laboratories. OVA D1 mouse mesenchymal stem cells, phosphate buffered saline 10×, and Hank's Balanced Salt Solution (HBSS) were purchased from Life Technologies. Cell culture media was prepared using Dulbecco's Modified Eagle Medium (DMEM) from Gibco, fetal bovine serum from Atlanta Biologicals, and penicillin streptomycin (10 000 units/mL) and 10 000 µg/mL streptomycin from Sigma Aldrich. Calcein AM (50 µg and 994.87 M) and Ethidium homodimer-1 (2 mM solution, 200 µL, MW 856.77) were purchased from Molecular Probes Life Technologies. The explanted pig lung was purchased from a butcher shop. The pig used for the in vivo testing was obtained from the Beth Israel Deaconess Animal Facility.

Equipment

The StratoSmart software was used to operate a dip coater by nanoStrata Inc. to prepare the layer-by-layer assemblies. Eggsnow USB Borescope Endoscope Pipe Inspection Camera—5.5 mm-2M) was purchased from Amazon. The Olympus Bronchoscope (EXERA BF-160) used in the in vivo bronchoscopy experiments is part of the clinical setup at Beth Israel Deaconess Medical Centre. Cell culture microscopy was performed using the Carl Zeiss Axiovert 40 CFL brightfield and fluorescent microscope. UV cleaning in the toxicity study was performed using the Hoefer UVC500-115V.

Preparation of the Coated Coverslips 6 mm circular glass coverslips were cut from a square 1"×2" square coverslip (1.5 thickness) using a diamond scriber. Glass substrates were treated with oxygen plasma (Model femto, Plasma Diener, Germany) for 2 min with 10 sccm oxygen gas flow and 100 W power to activate the silica surface. The layer-by-layer deposition was performed by immersion of the substrates in a 0.1 wt.-% solution of poly(diallyldimethylammonium) chloride (PDADMAC) for 10 min, followed by rinsing in DI water three times for 30 sec and subsequent immersion into a solution of 0.1 wt.-% Ludox silica colloids for 10 min and rinsing for 30 sec in water three times. This cycle was repeated to deposit 20 multilayers. The organic material was removed by combustion at 500° C. (ramped from room temperature to 500° C. for 5 h, 2 h at 500° C., ramped from 500° C. back to room temperature in 2 h. The resulting porous glass/silica coatings were functionalized by vapor-phase deposition of (1H,1H, 2H,2H-tridecafluorooctyl)-trichlorosilane or decyltrichlorosilane for 24 h at reduced pressure and room temperature. Prior to silanization, the substrates were plasma-treated with oxygen plasma as described above.

Attachment of the Coverslip to the Endoscope

Poly(dimethylsiloxane) was prepared at a 10:1 ratio of elastomer to curing agent using the Sylgard 184 Silicone Elastomer Kit. Bubbles were eliminated after mixing using a vacuum chamber. A drop of PDMS was applied to the tip of the scope and the coverslip gently placed on top. The PDMS was allowed to cure at room temperature for 48 hours prior to use.

Lubrication

3 µl of DuPont's KRYTOX™, Fluoromed's VITREON, or Gelest/Momentive silicone oil was added to the coverslip until uniform coverage was achieved by tilting. Holding a kim wipe to the edge of the coverslip and allowing the lubricant to absorb removed excess lubricant.

Blood Dip Experiments

Fresh porcine blood was incubated for 30 min in a 37° C. cell culture incubator prior to the experiment. A coated Eggsnow Borescope endoscope was dipped in the blood (approximately 1 sec per dip) and withdrawn. The image clarity was determined by visualizing a checkerboard pattern every ten dips. The image analysis is described in detail in the supplementary information.

Mucin Dip Experiments

Mucin powder from porcine stomach lining was resuspended in 1× Phosphate Buffered Saline at 17 wt. %. The solution was vortexed gently for 1 hour to ensure complete mixing. Coated Eggsnow scopes were dipped in the mucin solution, withdrawn and image clarity was determined by visualizing a checkerboard pattern after every dip. The image analysis performed was the same as for the blood dip experiments and is described in detail in the supplementary information.

Assessing Cell Toxicity

Silica Nanoparticles

Following ISO standard guidelines for in vitro toxicity tests, OVA D1 mesenchymal stem cells were cultured in DMEM medium supplemented with 10% FBS, antibiotic/antimycotic solution, sodium pyruvate, and bovine insulin following American Type Culture Collection established protocols. Apart from being commonly used in toxicity studies, MSCs were chosen as the cell line in an effort to generalize the toxicity to various tissues encountered in endoscopy. A confluent flask of cells was trypsinized and seeded in a 24-well plate at 100 000 cells/well. Cells were allowed to adhere for 24 hours in a cell culture incubator at 37° C., 5% $CO_2$ and 95% relative humidity. They were subsequently washed with HBSS buffer, and incubated with varying concentrations of silica nanoparticles (0 wt. %, 0.003 wt. %, 0.025 wt. %, 0.05 wt. %, and 1 wt. %) suspended in DMEM. Each concentration was performed in triplicate. The cells were incubated at 37° C. for another 24 hours. After this incubation period, the culture medium was removed from the wells and the cells washed with HBSS. 1 mL of DMEM solution (without serum) containing 0.5 µM Calcein AM and Ethidium homodimer-1 was added to each well. The cells were incubated in this solution for 20 min before imaging was performed with a Nikon inverted fluorescent microscope.

Silicone Oil/Fluorinated Oil

10 µL/cm$^2$ silicone oil was added to the layer-by-layer assembled silica nanoparticle coated glass surface that was cut in 0.5 cm×0.5 cm square pieces and spin coated at 5000 rpm for 1 min to remove excess lubricant. A droplet of water was added to the surface to check for slipperiness after spin coating. After confirmation that the samples were still slippery, the unlubricated glass samples and the lubricated samples were UV treated for 5 min and placed in a 24-well plate. Trypsinized mesenchymal stem cells were added to each well at 100 000 cells/well. Cells were allowed to adhere for 24 hours in a cell culture incubator at 37° C., 5% $CO_2$ and 95% relative humidity. The live/dead stain was performed after 72 hours using Calcein AM and Ethidium homodimer-1 was added at a 0.5 µM concentration in each well. The culture media was not removed prior to adding the live/dead stain in order to perform the staining in such a way that no cells would be removed from the wells. This particular method was used to obtain the results depicted in FIGS. 6A-6C. The toxicity data were collected slightly differently for FIGS. 11A-11B. Cells were seeded onto a transwell insert, which was placed into contact with the samples. The cells were stained after 24 hours. The brightfield images shown are of cells that were directly in contact with the coated substrate. This type of direct contact study was performed in an effort to satisfy the medical material in vitro toxicity tests outlined by the ISO standard guidelines.

Ex Vivo Lung Airway Inspection and Biopsy

The porcine model is frequently used in pulmonary research due to its similarities to humans in size and bronchial structures. The explanted porcine lung for the studies presented in FIG. 6A. was obtained from a butcher shop. A coated and uncoated Eggsnow Endoscope was used to visualize the inside of the lungs.

In Vivo Lung Biopsy

The animal was given general anesthesia and intubation with an 8.0-9.0 ET tube. It was mechanically ventilated with a bronchoscope adaptor to allow bronchoscopy. During this time, the animal was maintained in anesthesia with Fentanyl and propofol adjusted based on clinical signs (Fentanyl IV 50-100 µg/kg/hour for 2 hours Propofol IV 0.3-0.5 mg/kg/min for 2 hours).

The bronchoscope was introduced to perform airway inspections and biopsies. The endobronchial biopsy was performed with a standard biopsy forcep under direct visualization. A 1.8 mm forceps biopsy device was fed through the working channel (OD of 2 mm) on the bronchoscope (OD of 6.7 mm). The operator selected an area and the biopsy was done superficially with 1 single bite of the tissue (3 samples were collected). Three biopsies were performed using the coated bronchoscope in the left lung of a ventilated pig in vivo. The same three procedures were performed using an uncoated bronchoscope in the right lung.

During the transbronchial biopsy, the bronchoscope was advanced into the area of the lung to be biopsied. The forceps were advanced via the working channel and pushed out as far as possible. Then the forceps were retracted 1 cm to avoid a biopsy of the pleura. The forceps were opened, advanced and closed. They were then removed and the sample retrieved. This sequence was repeated 3 times. During the transbronchial brushing, the brush was advanced via the working channel while retracted in its protective sheath. Once the bronchoscope was advanced as far as possible into the area of the lung to be brushed, the brush in the protected sheath was pushed out of the working channel. Ten agitations were performed in the area of interest. Then the brush was retracted into its sheath (closed) and removed from the working channel and the procedure was repeated two more times.

The whole apparatus (bronchoscope and biopsy device) was retracted enblock via the ET tube. The coated bronchoscope was used first with 6 uL of silicone oil. All procedures involving the coated bronchoscope were performed in the left lung. The coverslip was then removed, the bronchoscope was wiped with a Clorox wipe, washed in ethanol, dried and re-inserted into the right lung where the same biopsy procedure was repeated with an uncoated bronchoscope. A blind study could not be performed because of a limitation to the number of bronchoscopes available for use. Therefore, only one bronchoscope could be used to test the performance of both the liquid-infused coating and the unmodified control.

In Vitro Characterization Using Pipe Inspection Endoscope

A 5.5 mm diameter pipe inspection camera was initially used to characterize the physico-chemical properties of the surface coating in the in vitro blood and mucus dips as well as the ex vivo lung experiment. These scopes were 5 mm in diameter and chosen to be similar in size to the bronchoscopes used in the in vivo experiments. A glass coverslip was coated and attached on the surface of the camera using PDMS (FIGS. 1A-1B). The subsequent in vivo experiments were performed using a 6.7 mm diameter bronchoscope that was modified with a 6 mm glass coverslip cut in the shape of a crescent to fit over the camera lens and light sources leaving the working channel exposed (FIGS. 1C-1D). The coverslip was coated with the liquid-infused coating and attached onto the bronchoscope using PDMS. Three coated bronchoscopes were used and operated by three physicians. All the procedures were repeated multiple times.

Image Analysis for Blood and Mucus Dip Experiments

ImageJ was used to subtract the background of the image at a threshold of 10 pixels. The following options were checked: light background, separate colors, sliding paraboloid, disable smoothing. The image was converted from FIGS. 7A and 7B.

Matlab was used to count the number of excess white pixels, which corresponds to the area obscured assuming that an unobstructed image would have approximately 50% black pixels and 50% white pixels. The following script outputs values for the excess white region.

```
clear all
clc
Folder='/Users/steffisunny/Documents/Aizenberg Group/Endoscope
Project/All Blood Dip Experiments/500cSt silicone oil_06-10-15';
i=0;
for imagenum=0:10:100
i=i+1;
    Picture = [Folder,'/',num2str(imagenum),'_6_imageJ10.jpg'];
original=imread(Picture);
greyimg=[ ]
greyimg = im2bw(original, graythresh(original));
numberOfPixels(i) = numel(greyimg);
numberOfBlackPixels(i) = sum(sum(greyimg == 0));
numberOfWhitePixels(i) = sum(sum(greyimg));
percentwhite(i)=numberOfWhitePixels(i)/numberOfPixels(i)*100
percentblack(i)=numberOfBlackPixels(i)/numberOfPixels(i)*100
approximateblurredregion(i)=percentwhite(i)−percentblack(i)
end
```

Re-Lubrication of 10 cSt Silicone Oil

After 100 dips in whole porcine blood, the pipe inspection endoscope was gently rinsed, re-lubricated and dipped in whole porcine blood another 100 times. FIG. 8 demonstrates the clarity of dips 0, 20, 40, 60, 80, and 100 after re-lubrication.

Blood Submersion with Fluorinated Oils

Figure 9A:
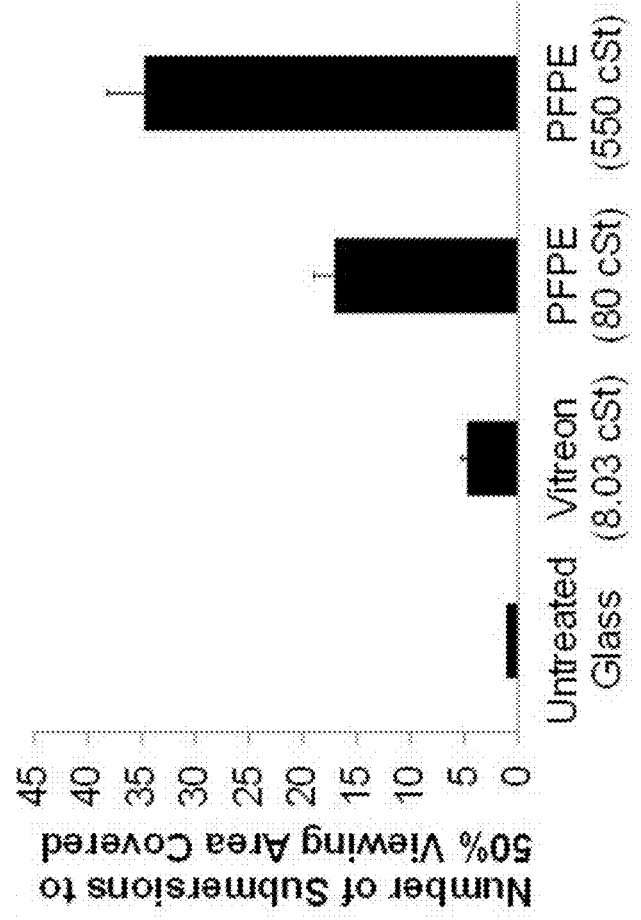
FIGS. 9A-9C show blood submersion with fluorinated oils. Whole porcine blood dipping experiments with varying viscosity of fluorinated lubricants. All experiments were performed with a sample repeat of three.
Figure 9B:
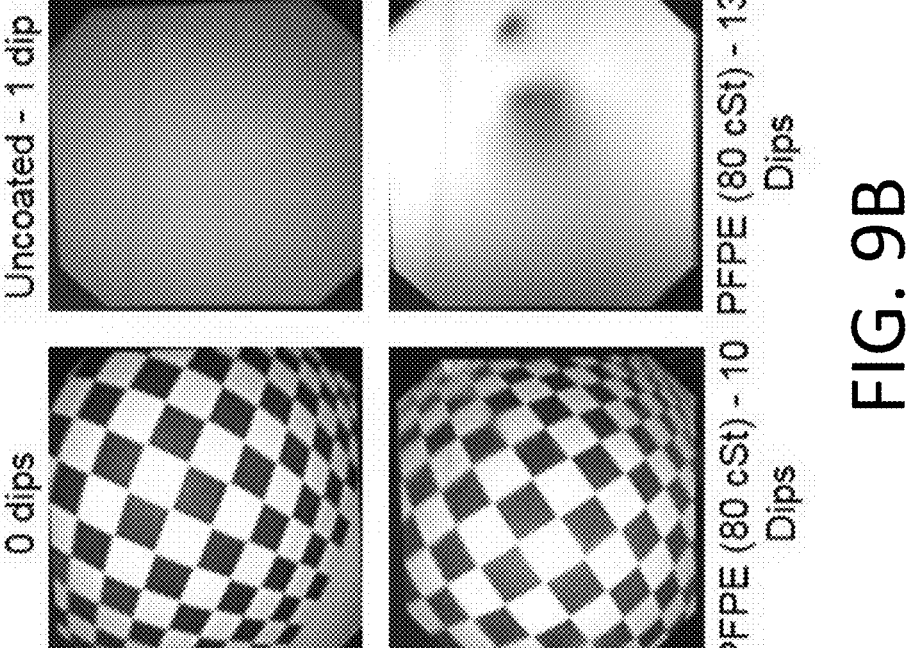
Figures 10A, 10B:
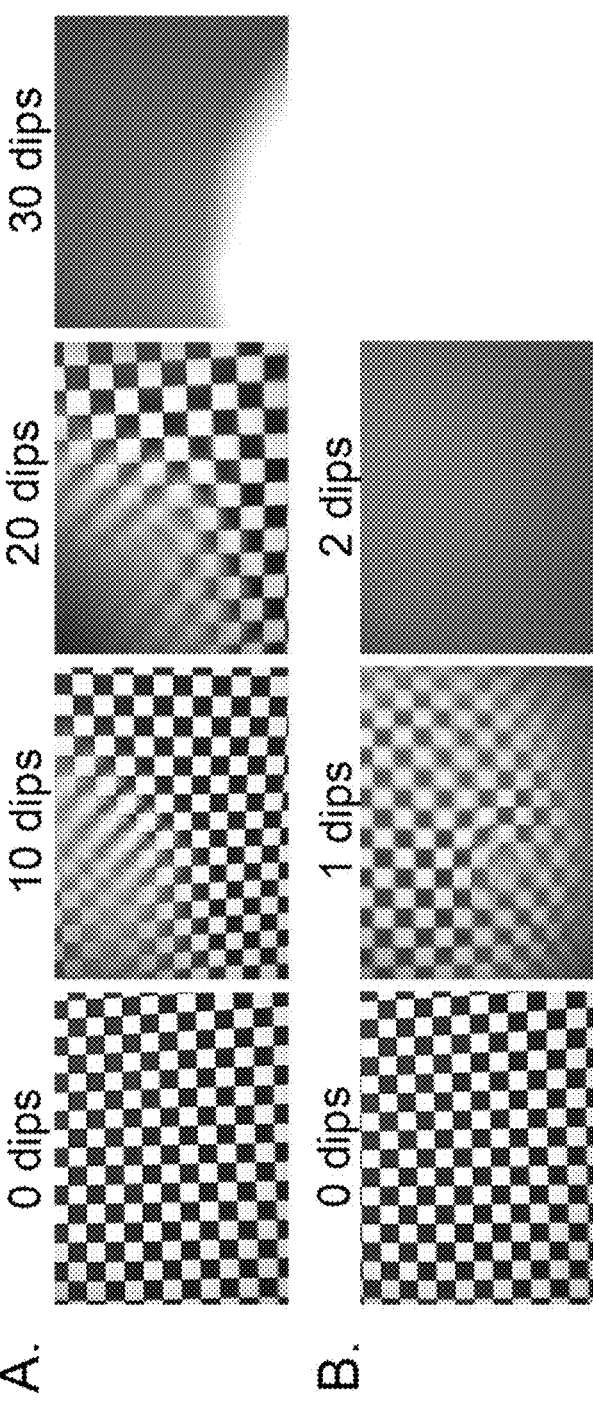
FIGS. 10A-10B show silicone oil and fluorinated oils on un-functionalized silica layers. Dipping was performed in whole porcine blood using scopes coated with 20 layers of silica particles and (FIG. 10A) 10 cSt silicone oil and (FIG. 10B) PFPE 80 cSt. The silica particles were not functionalized.

The VITREON-infused coating maintains 100% visibility for four dips in whole porcine blood at which point fifty percent of the visual field is occluded by blood FIG. 9A). However, reminiscent of what occurs during endoscopic procedures, the uncoated endoscope fails instantly. Higher viscosity perfluorocarbons were tested and determined to increase the longevity of the coating. The commercially available perfluoropolyether, KRYTOX™ 105 (550 cSt) outperforms VITREON (8 cSt) and KRYTOX™ 103 (80 cSt) by approximately 29 dips and 19 dips respectively.

Figure 9C:
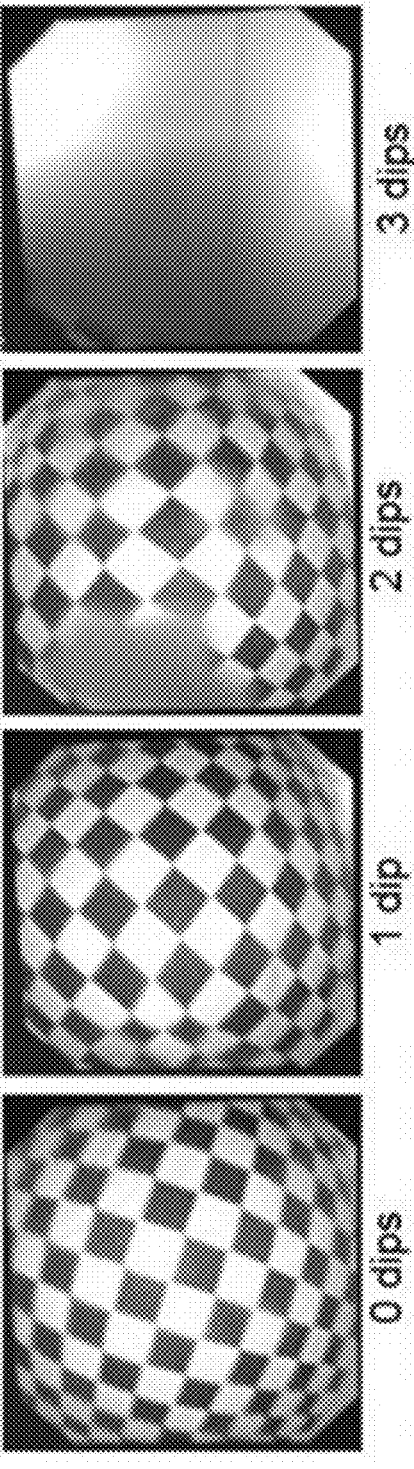

In contrast to the silicone oils, after a pinning point forms on the fluorinated coating, complete loss in visibility occurs almost immediately. A wash with de-ionized water and re-lubrication only leads to continued clarity for three more dips before failure occurs again, indicating a compromised surface functionality, presumably from adsorption of proteins (FIG. 9C). On the other hand, the silicone oil coatings (10 cSt) survive for over twice the number of dips, or over 95 dips longer, when compared to the fluorinated oil VITREON at a similar viscosity (8 cSt).

Figure 11A:
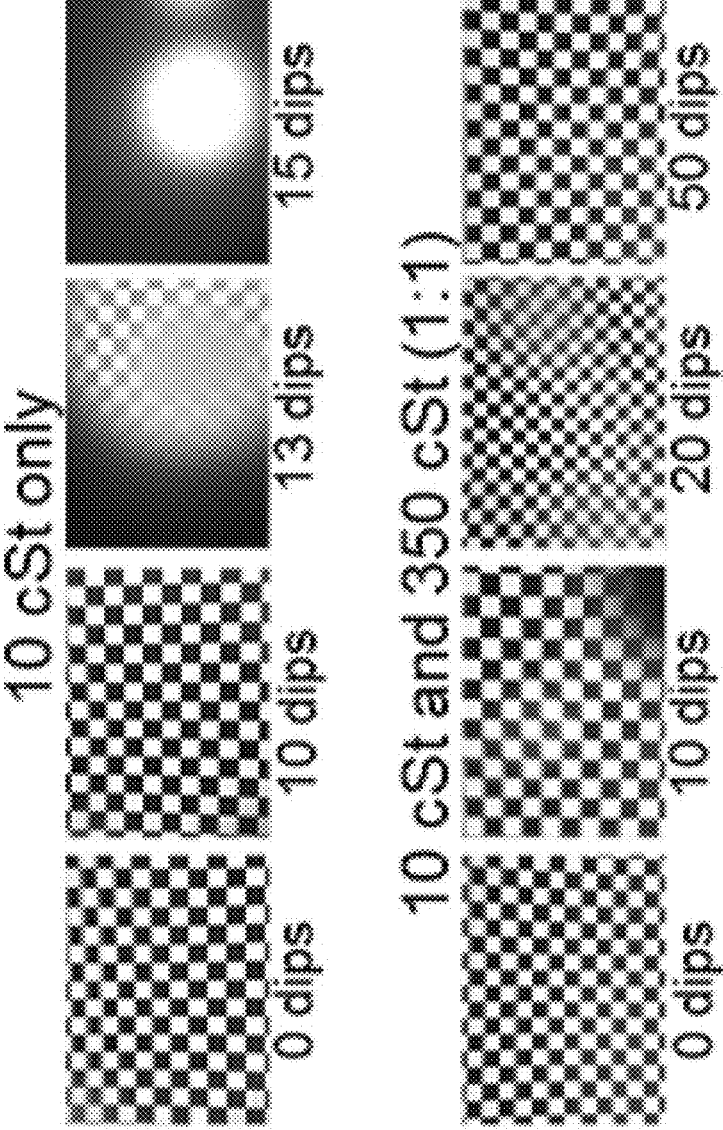
FIGS. 11A-11B show the difference in longevity between 10 cst silicone oil and 350 cst silicone oil.
Figure 11B:
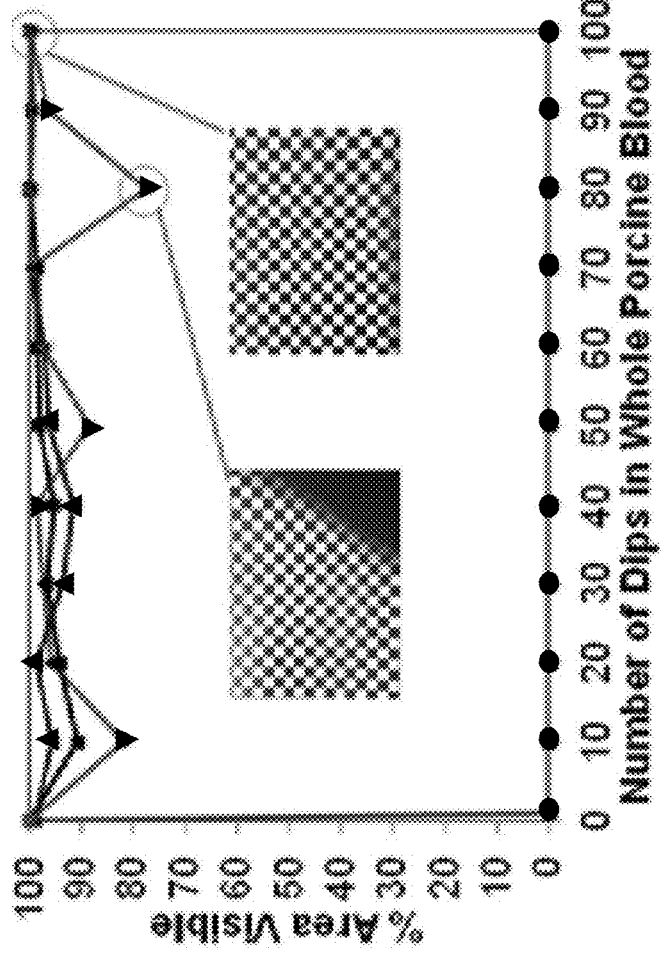
Figures 12A, 12B, 12C:
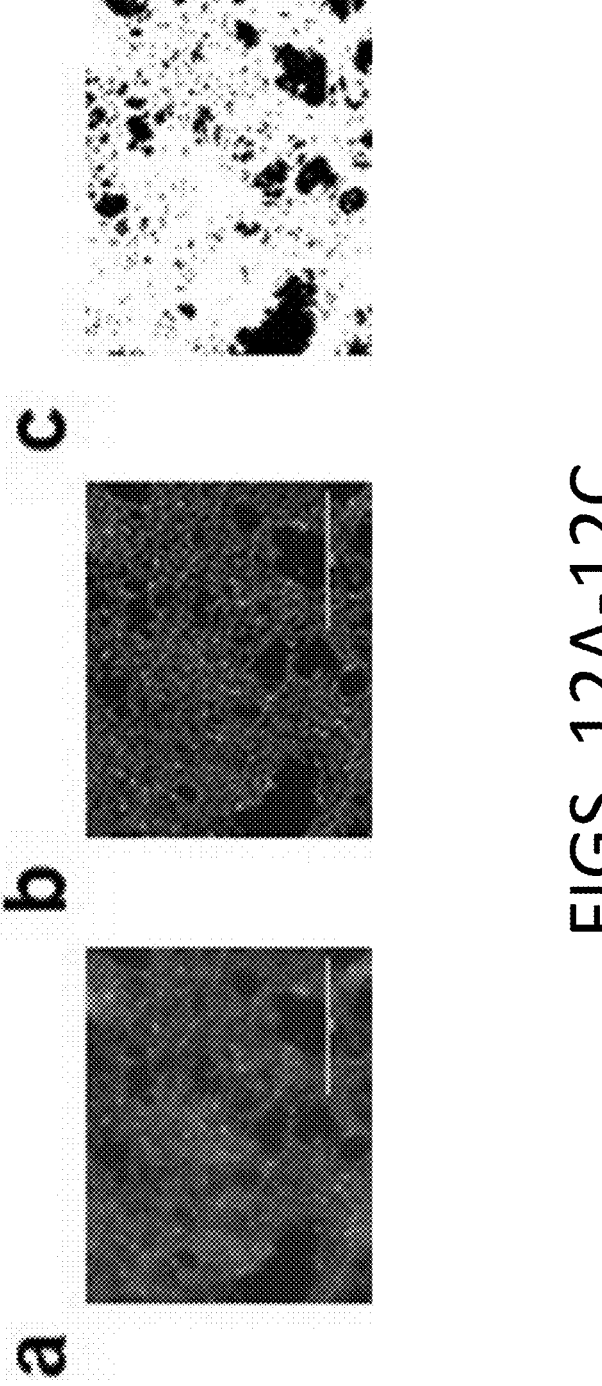
FIGS. 12A-12C show the image analysis for toxicity experiments. The original image (FIG. 12A) is changed to a grey scale with enhanced local contrast (FIG. 12B). Using auto threshold, the cell coverage is output in white (FIG. 12C).

The discrepancy in longevity between the two coatings can be explained by the differences in matching surface chemistry. A vapor phase deposition of fluorosilane is used to create a monolayer of fluoroalkyl chains that disguise the underlying silica particles allowing for infiltration and spreading of a perfluorocarbon oil. However, when introduced to multiple air water interfaces lubricant de-wetting and depletion leads to the ultimate failure of the coating. The same vapor phase deposition of hydrophobic alkyl chains results in a surface with a combination of silica surface chemistry and the hydrophobic alkyl chains which more closely matches the chemistry of the silicone oil allowing for improved lubricant retention upon exposure to a liquid-air interface and therefore, increased longevity. This is demonstrated with a lubricant-infused coating prepared without matching the surface chemistry of the silica nanoparticles to the chemical nature of the lubricant. When silicone oil is infused into the silica nanoparticle coating, its native surface functionality appears to be sufficient for the oil to remain entrapped for 20 dips in blood before the repellency properties fail (using dodecyl-silane surface functionality, the same coating survives for upwards of 100 dips). The same silica particle coating without surface functionalization infused with perfluorocarbon oil fails almost instantly indicating that there is no matching surface chemistry between the oil and the coating to ensure coating longevity (FIG. 8). Difference in Longevity Between 10 cSt Silicone Oil and 350 cSt Silicone Oil Typically in flexible bronchoscopy, the endoscope may be simultaneously used for both therapeutic purposes such as clearing a mucus plug and diagnostic purposes such as biopsies from lymph nodes, which typically leads to blood release within the lungs. This combined interaction with both mucus and blood can deteriorate the longevity of the coating. In order to mimic this scenario, we re-lubricated the endoscopes after the dipping experiments in mucus and performed another series of blood exposure. As shown in FIG. 11A, the 10 cSt oil fails at 13 dips while the 350 cSt oil sustains clarity for 50 dips. This indicates that despite 10 cSt silicone oil typically outperforming the higher viscosity oils, there may be occasions when choosing a higher viscosity lubricant is beneficial depending on the procedure and the predicted severity of the fouling.

Approximate Calculation of Number of Silica Particles on Coating

As shown by Sunny et al using Quartz Crystal Microbalance data, 10 layers of silica particles consist of roughly less than $1.2 \times 10^4$ ng/cm$^2$. It is estimated that on a 6 mm diameter coverslip containing 20 layers of particles, there will be roughly $6.8 \times 10^{-6}$ g of particles. This corresponds to 0.00068 wt. %. However, it should be kept in mind that a bronchoscope has a 2 mm working channel that is not coated. Therefore, this value is an over-estimation.

Image Analysis for Toxicity Experiments

A macro file was created in ImageJ containing the following commands:

run("8-bit");
    run("Enhance Local Contrast (CLAHE)", "blocksize=25
        histogram=2048 maximum=20 mask=*None*fast (less
        accurate)");
    run("Auto Threshold", "method=MinErrorl white"); run
        ("Select All");
    run("Measure");

The command Measure returns the % Area value of the white regions. The same process is performed for the dead stain in red. However, the auto threshold method used for this stain is Triangle.

Toxicity of PFPE (80 cST)

Toxicity study of PFPE (80 cSt) infused layer-by-layer (LbL) assembled silica particle surfaces. Brightfield images show mesenchymal stem cells that were in contact with plain glass and PFPE infused LbL surfaces for 24 hours of incubation. Calcein AM is used to stain live mesenchymal stem cells grown on a polymer mesh in contact with plain glass and PFPE infused LbL glass in a transwell plate. Cells thrive in the presence of both the plain glass control and the liquid-infused coating. There are negligible dead cells. (See FIG. 13).

Example 2

There is a growing interest in miniaturizing endoscopes to visualize the most inaccessible regions of the human body. Bronchoscopes are unable to image the narrowest regions of the airway which are less than 2 mm in diameter. While cameras of this size exist that can be used to image these airways, they lack the external control required to maneuver them. Further miniaturization of currently used scopes is impossible, as it will necessitate the elimination of the working channel, leaving doctors without the currently existing recourse of suction and irrigation to clear the visual field. The results described in Example 1 above demonstrate that immersions in blood, mucus and secretions do not compromise an uninterrupted airway inspection with the scope coated in a transparent, repellent, oil-infused coating. The presence of such a coating offers an unprecedented opportunity to design a flexible instrument without working channels, reducing its size down to 2-3 mm, approximately the diameter of un-imaged small airways. Liquid-infused coatings provide a strategy to significantly expand the limits of the areas of the human body that physicians can image, offering enormous potential for the improvement of disease diagnosis and treatment.

As shown in FIG. 2A, a guidewire comprising a miniature camera that is coated with a repellent, oil-infused coating is threaded through an existing working channel of an endoscope. As shown in FIG. 2B, the guidewire and miniature camera are less than 2 mm in diameter and are threaded through an existing working channel into a narrow-diameter hole or opening with a diameter of 2 mm or more. For example, the miniature camera can fit into narrow pathways such as bronchioles (FIG. 2B), allowing for visual inspection. The miniature camera comprises a CMOS or CCD chip at the distal end that electronically transmits images and is coupled with a light source that is transmitted via a fiber optic bundle. The miniature camera comprises or is modified to comprise a porous surface layer that is optically transparent and light transmissive. In some embodiments, the surface structure of the roughened or porous surface layer comprises feature sizes that are under the diffraction limit. In some embodiments, the surface structure of the roughened or porous surface layer comprises feature sizes that are under 1 µm. Infiltration of the surface layer with a low surface energy liquid creates an ultra-smooth surface that is slippery and resists or reduces adhesion by particles and immiscible liquids.

Example 3

Figure 14:
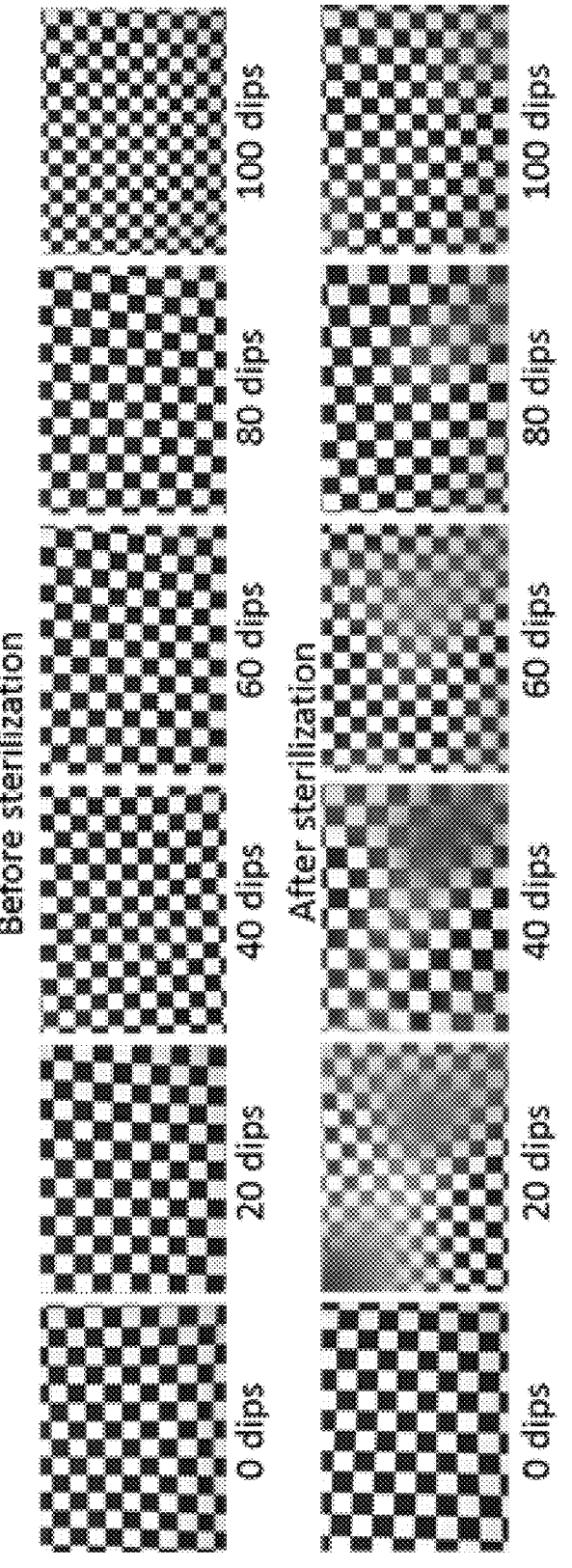
FIG. 14 illustrates that the visible field of an endoscope dipped in porcine blood remains substantially clear even after sterilization.

One of the main concerns with coatings is their ability to survive reprocessing procedures for sterilization. Chemical sterilization is commonly used in lieu of thermal treatments, which can damage sensitive electronics, and gas treatments like ethylene oxide, which is time consuming (over 12 hours of reprocessing). To address sterilization concerns in reuseable endoscopes, the layer-by-layer silica SLIPS coated endoscope was submerged in a 7.5% hydrogen peroxide solution, which is an FDA approved sterilization solution (https://www.cdc.gov/hicpac/disinfection_sterilization/3_0disinfectequipment.html), for 20 min after dipping in porcine blood one hundred times. A checkerboard pattern is imaged by the endoscope to assess visualization. After this submersion, the endoscope was rinsed with DI water and re-lubricated. The endoscope was once again subjected to one hundred dips in porcine blood. As shown in FIG. 14, the visible field remains clear at the end of one hundred dips despite some variability in visualization at 20, 40, and 60 dips. In the case of single-use endoscopes, the coating would only need to survive the duration of the procedure. Such endoscopes include, but are not limited to, capsule endoscopy, single use laryngoscopes, and single use bronchoscopes, and are manufactured by a variety of companies. Coating protective disposable covers for endoscopes (an example is the EndoSheath sold by Cogentix) are also a possibility for applying this coating.

Upon review of the description and embodiments provided herein, those skilled in the art will understand that modifications and equivalent substitutions may be performed in carrying out the invention without departing from the essence of the invention. Thus, the invention is not meant to be limiting by the embodiments described explicitly above.

What is claimed is:

1. An endoscope, comprising:

an insertion tube and a proximal body, the insertion tube starting from the proximal body and having a distal end;

at the distal end of the insertion tube;

an illumination source designed to project light from an illumination emitter at the distal end of the insertion tube, and an image collector designed to collect light to form an image of objects at the distal end; and a substrate designed to seal the distal end to exclude tissues and bodily fluids from interference with the image collector during endoscopy, the substrate designed to entrain a lubricating fluid on a wetting surface, the substrate, wetting surface, and lubricating fluid to form a protective and transparent window over the image collector, the wetting surface lying on the side of the substrate facing outwardly from the image collector into a cavity for examination by the endoscope, the wetting surface formed by deposition of silica particles or other inorganic oxide nanoparticles onto the substrate, followed by heating to form a porous solid, the substrate's wetting surface designed to entrain a lubricating fluid at the distal end of the insertion tube, the lubricating fluid being immiscible with the bodily fluids, the wetting surface being designed to present wetting to the lubricating fluid preferentially relative to the bodily fluids, the wetting surface and the wetting it presents being designed to entrain the lubricating fluid in a layer that is ultra-smooth, slippery, and optically transparent over the wetting surface during exposure to the tissues and bodily fluids.

2. The endoscope of claim 1, wherein the lubricating fluid comprises silicone oil, or mixtures thereof.

3. The endoscope of claim 2, wherein the lubricating fluid comprises a mixture of silicone oils of different viscosities.

4. The endoscope of claim 1, wherein the lubricating fluid is a perfluoropolyether.

5. The endoscope of claim 1, wherein the wetting surface is functionalized by a coating to accept wetting by and to retain the lubricating fluid.

6. The endoscope of claim 5, wherein the wetting surface is functionalized to accept wetting by and to retain the lubricating fluid by a coating of partially or fully fluorinated alkyl chains using chlorosilane coupling, amide coupling, or glicydyl chemistry which is reactive with the surface of the substrate.

7. The endoscope of claim 6, wherein the wetting surface is functionalized to accept wetting by and to retain the lubricating fluid by a coating of (1H, 1H, 2H, 2H-tridecafluorooctyl)-trichlorosilane.

8. The endoscope of claim 1, wherein the substrate is integral with an optical lens for the image collector.

9. The endoscope of claim 1, wherein the substrate is not integral with an optical lens for the image collector.

10. The endoscope of claim 9, wherein the substrate is a disposable component reversibly secured to a distal window of the endoscope.

11. The endoscope of claim 1, wherein the wetting surface is a porous surface of the substrate, the substrate being solid, the porosity designed to preferentially accept wetting by and to retain the lubricating fluid relative to the bodily fluids.

12. The endoscope of claim 11, wherein the wetting surface is formed by nanoparticles.

13. The endoscope of claim 12, wherein the lubricating fluid is silicone oil and mixtures thereof.

14. The endoscope of claim 1, wherein the wetting surface is functionalized to accept wetting by and to retain the lubricating fluid by a coating of a hydrocarbon group, and the hydrocarbon group is linear, branched, or combinations thereof.

15. The endoscope of claim 1, wherein the lubricating fluid is selected from the group consisting of a perfluorinated fluid, tertiary perfluoroalkylamine, perfluorotri-n-pentylamine, perfluorotri-n-butylamine, a perfluoroalkylsulfide, a perfluoroalkylsulfoxide, a perfluoroalkylemer, a perfluorocycloether, a perfluoropolyether, a perfluoroalkylphosphine, a perfluoroalkylphosphmeoxides, a polydimethylsiloxane, functional modifications of polydimethylsiloxane, partially or fully fluorinated oils, and mixtures thereof.

16. The endoscope of claim 15, wherein the lubricating fluid is perfluoroperhydrophenanthrene or perfluorodecalin.

17. The endoscope of claim 1, wherein the image collector includes a CMOS or CCD chip.

18. The endoscope of claim 1, wherein the image collector includes a rod lens imaging lens.

19. The endoscope of claim 1, wherein the image collector includes a fiber optic image collector.

20. The endoscope of claim 1, wherein the illumination source includes a fiber optic illumination system.

21. The endoscope of claim 1, wherein the lubricating fluid is selected from the group consisting of food-grade oil, food compatible liquids, olive oil, canola oil, coconut oil, corn oil, rice bran oil, cottonseed oil, grape seed oil, hemp oil, mustard oil, palm oil, peanut oil, pumpkin seed oil, safflower oil, and mixtures or combinations thereof.

22. The endoscope of claim 1, wherein the image collector includes a camera.

23. An optically transparent article, comprising:

a transparent substrate having a wetting surface designed to entrain a layer of a lubricating fluid on the wetting surface;

the substrate being designed to be affixed to a distal end of an insertion tube of an endoscope, the shape and affixation of the substrate being designed to:

form an operable endoscope tip with the distal end during endoscopy, seal to exclude tissues and bodily fluids from interference with an image collector of the endoscope during endoscopy, and present the substrate at the distal end with its wetting surface facing outwardly from the image collector into a cavity for examination by the endoscope;

the lubricating fluid layer being immiscible with biological material and bodily fluids to which the endoscope distal end is to be exposed;

the wetting surface designed to present high wetting to the lubricating fluid preferentially relative to bodily fluids to which the endoscope distal end is to be exposed, the wetting surface formed by deposition of silica particles or other inorganic oxide nanoparticles onto the substrate, followed by heating to form a porous solid designed to entrain the lubricating fluid in a layer to form an ultra-smooth, slippery, optically transparent layer over the wetting surface during exposure to the tissues and bodily fluids;

the substrate, wetting surface, and lubricating fluid being designed to form a sealed, protective and transparent window over the image collector at the distal end of the endoscope.

24. The optically transparent article of claim 23, wherein:

the substrate and wetting surface are designed with the lubricating fluid to form a protective and transparent window over the image collector.

\* \* \* \* \*